US007416856B2

(12) United States Patent
Baliga et al.

(10) Patent No.: US 7,416,856 B2
(45) Date of Patent: *Aug. 26, 2008

(54) HIGH SENSITIVITY ASSAY FOR DETECTION OF NUCLEOSIDE DIPHOSPHATE PRODUCTION

(75) Inventors: Ramesh Baliga, Foster city, CA (US); Donglin Guo, Fremont, CA (US); Daniel W. Pierce, Hayward, CA (US); Jeffrey T. Finer, Foster City, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 184 days.

This patent is subject to a terminal disclaimer.

(21) Appl. No.: 11/296,193

(22) Filed: Dec. 6, 2005

(65) Prior Publication Data

US 2006/0257962 A1    Nov. 16, 2006

Related U.S. Application Data

(60) Continuation-in-part of application No. 11/270,193, filed on Nov. 8, 2005, now Pat. No. 7,202,051, which is a continuation of application No. 10/856,580, filed on May 28, 2004, now abandoned, which is a continuation of application No. 10/106,665, filed on Mar. 25, 2002, now Pat. No. 6,743,599, which is a continuation of application No. 09/724,990, filed on Nov. 28, 2000, now abandoned, which is a division of application No. 09/314,464, filed on May 18, 1999, now Pat. No. 6,410,254.

(51) Int. Cl.
*C12Q 1/42* (2006.01)
(52) U.S. Cl. .............................. 435/21; 435/15; 435/16; 435/17; 435/18; 435/19; 435/196
(58) Field of Classification Search .................. 435/21, 435/15–19, 196
See application file for complete search history.

(56) References Cited

U.S. PATENT DOCUMENTS

| 4,923,796 | A |   | 5/1990 | Deneke et al. |        |
|-----------|---|---|--------|---------------|--------|
| 5,283,173 | A |   | 2/1994 | Fields et al. |        |
| 5,525,490 | A |   | 6/1996 | Erickson et al.|       |
| 5,667,973 | A |   | 9/1997 | Fields et al. |        |
| 5,673,463 | A |   | 10/1997| Chih-wen      |        |
| 5,759,795 | A |   | 6/1998 | Jubin         |        |
| 6,207,403 | B1|   | 3/2001 | Goldstein et al.|      |
| 6,410,254 | B1| * | 6/2002 | Finer et al.  | 435/21 |
| 6,743,599 | B1| * | 6/2004 | Finer et al.  | 435/21 |
| 7,202,051 | B1| * | 4/2007 | Finer et al.  | 435/21 |

OTHER PUBLICATIONS

Banik et al., "A continuous fluorimetric assay for ATPase activity," Biochem. J., 266:611-614 (1990).
Brune et al., :Direct, real-time measurement of rapid inorganic phosphate release using a novel fluorescent probe and its application to actomyosin subfragment 1 ATPase, Biochem., 33:8262-8271 (1994).
Chien et al., "The Two-hybrid system: A method to identify and clone genes for proteins that interact with a protein of interest," PNAS USA, 88: 9578 9582 (1991).
Dang et al., "Intracellular Lecucine Zipper Interactions Suggest c-Myc Hetero Oligomerization" Mol. Cell. Bio., 11:954-962 (1991).
Desai et al., "Kin I Kinesins are microtubule-destablizing Enzymes," Cell, 96:69-78 (1999).
Fearon et al., "Karyoplasmic interaction selection strategy: A general strategy to detect protein-protein interactions in mammalian cells," PNAS USA, 89:7958-7962 (1992).
Fields et al., "A novel genetic system to detect protein-protein interactions," Nature, 340:245-246 (1989).
Fiske et al., "The colorimetric determination of phosphates," J.Bio. Chem., 66:375-400 (1925).
Funk, et al., "Development of high-throughput screens for discovery of kinesin adenosine triphosphatase modulators," Analytical Biochemistry329:68-76 (2004).
Goldstein, "With apologies to Scheherazade: Tails of 1001 Kinesin Motors," Annu. Reb. Genet., 27:319-351 (1993).
Greengard, "Determination of intermediary metabolites by enzymic fluorimetry," Nature, 178:632-634 (1956).
Hackney, "The rate-limiting step in microtubule-stimulated ATP Hydrolysis by Dimeric Kinesin Head Domains Occurs while bound tot he microtubule," J. Biol. Che., 269(23):16508-16511 (1994).
Huang et al., "Drosophila kinesin minimal motor domain expressed in *Escherichia coli*," JBC, 269 (23): 16493-16501 (1994).
Rieger et al., "A continuous spectrophotometric assay for asparte transcarbamylase and ATPases," Anal., Biochem., 246:86-95 (1997).
Ronaghi et al., "Real-time DNA Sequencing Using Detection of Pyrophosphate Release," Analytical Biochemistry, 242: 8-89 (1996).
Ronaghi et al. "A Sequencing method based on real-time pyrophosphate", science 1998, pp. 363-365, vol. 281.
Schindler, et al., "Identification of Two New Inhibitors of the Hepatic Glucose-6-Phosphatase System," Drug Development Research 44:34-40 (1998).
Stedman's Medical Dictionary, p. 1404, 26th Edition, Williams & Wilkins, A Waverly Company.
Ungerer et al., "An enzymatic assay of inorganic phosphate in serum using nucleoside phosphorylase and zanthine oxidase," Elsevier Clinica Chimic Act., 223: 149-157 (1993).
Vasavada et al., "A contingent replication assay for the detection of protein protein interactions in animal cells," PNAS USA, 88:10686-10690 (1991).
Vazquez, et al., "Determination of phosphate in nanomolar range by an enzyme-coupling fluorescent method," Analytical Biochemistry 320:292-298 (2003).
Walczak et al., "XKCMI: A xenopus kinesin-related protein that regulates microtubule dynamics during mitotic spindle assembly," Cell, 84:37-47 (1996).
Webb, "A continuous spectrophotometric assay for inorganic phosphate and for measuring phosphate release kinetics in biological systems, "PNAS USA, 89-4884-4887 (1992).
Wood et al., "Plus End-Directed Microtubule Motor Required for Chromosome Congression," PCT application claiming priority to U.S. Appl. No. 60/058,645, filed Sep. 11, 1997.

* cited by examiner

*Primary Examiner*—Tekchand Saidha
(74) *Attorney, Agent, or Firm*—Townsend and Townsend and Crew LLP

(57) ABSTRACT

The present invention provides assays for detecting ADP, GDP and inorganic phosphate. These assays can be used directly to detect the presence of ADP, GDP and inorganic phosphate or can be used as part of a number of methods for identifying candidate agents that bind to a target protein or serve as modulators of the biological activity of a target protein.

21 Claims, 4 Drawing Sheets

HIGH SENSITIVITY ASSAY FOR DETECTION OF NUCLEOSIDE DIPHOSPHATE PRODUCTION

CROSS-REFERENCES TO RELATED APPLICATIONS

This application is a continuation-in-part of U.S. application Ser. No. 11/270,193, filed Nov. 8, 2005, now U.S. Pat. No. 7,202,051, which is a continuation of U.S. application Ser. No. 10/856,580, filed May 28, 2004, now abandoned, which is a continuation of U.S. application Ser. No.10/106,665, filed Mar. 25, 2002, now U.S. Pat. No. 6,743,599, which is a continuation of U.S. application Ser. No. 09/724,990, filed Nov. 28, 2000, abandoned, which is a division of U.S. application Ser. No. 09/314,464, filed May 18, 1999, now U.S. Pat. No. 6,410,254, each of which is incorporated herein by reference in its entirety for all purposes.

FIELD OF THE INVENTION

This invention is related to the use of adenosine diphosphate (ADP), guanosine diphosphate (GDP), or phosphate in assays for identifying candidate agents that bind to or modulate the binding characteristics or biological activity of a protein.

BACKGROUND

Drugs and other compounds intended for use in the diagnosis, cure, mitigation, treatment or prevention of disease in man or other animal or for use in the agricultural arena, have made a significant impact on the practice of modern medicine and on the agricultural arena. In some cases, such as in the development of vaccines, drugs have essentially eradicated once untreatable diseases. In the case of the agriculture, compounds have been developed which both extend the life and/or volume of produce as well as kill unwanted plants where desirable. Therefore, the development of these compounds is of great interest.

Many useful compounds modulate the physical interaction of proteins. Traditionally, these protein-protein interactions have been evaluated using biochemical techniques, including chemical cross-linking, co-immunoprecipitation, co-fractionation and co-purification. Recently genetic systems have been invented to detect protein-protein interactions. The first work was done in yeast systems, and was termed the "yeast two-hybrid" system. The basic system requires a protein-protein interaction in order to turn on transcription of a reporter gene. Subsequent work was done in mammalian cells. See Fields et al., Nature 340:245 (1989); Vasavada et al., PNAS USA 88:10686 (1991); Fearon et al., PNAS USA 89:7958 (1992); Dang et al., Mol. Cell. Biol. 11:954 (1991); Chien et al., PNAS USA 88:9578 (1991); and U.S. Pat. Nos. 5,283,173, 5,667,973, 5,468,614, 5,525,490, and 5,637,463.

In another approach to drug discovery, studies are designed to determine the biological activity of a protein. For example, the conditions such as the specific substrate or stimulator required for an enzymatic reaction are investigated. Moreover, there are a number of studies designed specifically to aid in the detection step in these assays. For example, one study discloses a spectrophotometric assay for inorganic phosphate (Pi) to probe the kinetics of Pi release from biological systems such as GTPases and ATPases. Webb, PNAS 89:4884-4887 (1992). Another study reports on an enzymatic assay of inorganic phosphate in serum using nucleoside phosphorylase and xanthine oxidase. Ungerer et al., Elsevier Clin. Chim. Acta 223:149-157 (1993). A continuous spectrophotometric assay for aspartate transcarbamylase and ATPases is reported in Rieger et al., Anal. Biochem. 246:86-95 (1997). There is also a study that reports on the measurement of inorganic phosphate release using fluorescent probes and its application to actomysin subfragment 1 ATPase. Brune et al., Biochem. 33:8262-8271 (1994). U.S. Pat. No. 4,923,796 discloses a method for quantitative enzymatic determination of ADP. Microtubule-stimulated adenosine triphosphate (ATP) hydrolysis by kinesin is discussed in Hackney, J. Biol. Chem. 269(23):16508-16511 (1994). Furthermore, enzymatic fluorimetry and fluorimetric assays for ATPase activity are reported on in Greengard, Nature 178:632-634 (1956) and Utpal and Siddhartha, Biochem. J. 266:611-614 (1990), respectively.

In a different approach, modulators of an enzymatic reaction are investigated, wherein the conditions that allow the enzymatic reaction to occur are already known. For example, U.S. Pat. No. 5,759,795 discloses an assay for identifying an inhibitor of a Hepatitis C Virus NS3 protein ATPase which involves a luciferase reaction. Luciferase reactions are known in the art. In the case of an ATPase inhibitor, the presence of an ATPase inhibitor is indicated when ATP is available to drive the oxidation of luciferin by luciferase. This approach requires ATP but does not re-generate ATP.

Thus, while efforts have been made toward drug discovery, more efficient means are desirable. In particular, there is a need for an efficient system which can distinguish between a compound directly binding to a second component, or whether the compound modulates the binding between two other components, or whether the compound modulates the biological activity of a known enzymatic reaction such as catalyzed by an ATPase or GTPase, for instance.

SUMMARY

The present invention provides methods which identify candidate agents that bind to a protein or act as a modulator of the binding characteristics or biological activity of a protein. In one embodiment, the method is performed in plurality simultaneously. For example, the method can be performed at the same time on multiple assay mixtures in a multi-well screening plate as further described below. Furthermore, in some embodiments, fluorescence or absorbance readouts are utilized to determine enzymatic activity. Thus, in one aspect, the invention provides a high throughput screening system.

In one embodiment, the present invention provides a method of identifying a candidate agent as a modulator of the activity of a target protein. The method comprises adding a candidate agent to a mixture comprising a target protein which directly or indirectly produces GDP, ADP or phosphate under conditions which normally allow the production of GDP, ADP or phosphate. The method further comprises subjecting the mixture to an enzymatic reaction which uses said GDP, ADP or phosphate as a substrate under conditions which normally allow the GDP, ADP or phosphate to be utilized and determining the level of activity of the enzymatic reaction. A change in the level between the presence and absence of the candidate agent indicates a modulator of the target protein.

In one aspect, the target protein indirectly produces the ADP, GDP or phosphate by producing a substrate for a reaction which produces ADP, GDP or phosphate. In another aspect, the target protein indirectly produces ADP, GDP or phosphate by regulating an enzyme which produces ADP, GDP or phosphate. In yet a further aspect, the target protein directly produces phosphate, ADP or GDP.

In another aspect, the invention provides a method of identifying a candidate agent as a modulator of the activity of a target protein wherein the target protein uses ADP, GDP or phosphate directly or indirectly. The method comprises adding a candidate agent to a mixture comprising the target protein under conditions which normally allow the utilization of ADP or phosphate. The method further comprises determining the level of utilization wherein a change in the level between the presence and absence of the candidate agent indicates a modulator of the target protein.

Certain methods that are provided, for example, are designed to identify a modulator of the activity of a target protein that can produce ADP. Some of these methods involve preparing a sample that includes a target protein, a candidate agent and an enzyme that utilizes ADP under conditions in which, in the absence of the candidate agent, the target protein can produce ADP. The activity of the enzyme is determined to determine the activity of the target protein. A change in the activity of the enzyme in the presence of the candidate agent relative to the activity of the enzyme in the absence of the candidate agent is an indication that the candidate agent is a modulator of the target protein.

Some of these assays for modulators of a target protein involve using a coupled enzyme system in which the utilization of ADP is coupled to the production of a detectable product. The coupled enzyme system can include, for example, a reaction in which the utilization of ADP by the enzyme results in the formation of pyruvate, a reaction in which the oxidation of pyruvate results in the formation of hydrogen peroxide, and a reaction in which the oxidation of hydrogen peroxide results in the conversion of a compound to the detectable compound.

In some assays, the sample can be prepared by combining the target protein, the candidate agent and the enzyme with phosphoenolpyruvate (PEP), pyruvate kinase (PK), pyruvate oxidase, phosphate and a peroxidase. The coupled enzyme system can include, for example, pyruvate kinase catalyzing the reaction between PEP and ADP formed by the target protein to form pyruvate and ATP, respectively; pyruvate oxidase in the presence of phosphate catalyzing the oxidation of pyruvate to acetylphosphate and the concomitant reduction of oxygen to hydrogen peroxide, and the peroxidase catalyzing the oxidation of hydrogen peroxide to superoxide and the concomitant reaction of the superoxide with the compound to form the detectable compound. In some methods, the activity of the enzyme can be determined in the form of a kinetic assay in which the activity of the enzyme is determined at multiple time points.

In some methods, the sample is prepared by contacting the target protein with a plurality of candidate agents. In some methods, the sample is prepared by contacting a plurality of target proteins with a plurality of candidate agents. For example, the sample can be prepared by preparing a plurality of samples, each sample containing the target protein and one or more of the plurality of candidate agents. The activity of the enzyme is determined for each of the plurality of samples.

The target protein can generate an initial product that regulates the production of ADP by another protein. The target protein also can generate a substrate for an enzyme that in turn produces ADP. The target protein also can be an activator of an ATPase.

In another approach, methods that are provided, for example, are designed to determine if a candidate agent is a modulator of the activity of a target protein that can produce or consume adenosine diphosphate (ADP). Some of these methods involve preparing a sample that includes a target protein, a candidate agent and an enzyme that utilizes ADP under conditions in which, in the absence of the candidate agent, the target protein can produce ADP. The production of ADP is then assayed using an enzymatic assay that utilizes ADP to determine the activity of the target protein. A change in the activity of the enzyme in the presence of the candidate agent relative to the activity of the enzyme in the absence of the candidate agent is an indication that the candidate agent is a modulator of the target protein.

In some assays, the activity of the enzyme is determined by detecting the formation of a detectable compound that has an extinction coefficient of at least 50,000 $M^{-1}cm^{-1}$ and is formed in a coupled enzyme system in which the utilization of ADP by the enzyme is coupled to formation of the detectable compound. In some assays, the coupled enzyme system includes a kinase that catalyzes a reaction between ADP and a phosphorylated substrate to form ATP and a dephosphorylated substrate, respectively, and involves coupling the oxidation of the dephosphorylated substrate to the formation of the detectable compound.

In another approach, methods that are provided, for example, are designed to determine if a candidate agent is a modulator of the activity of a target protein that can produce adenosine diphosphate (ADP). Some of these methods involve preparing a sample that includes a target protein, a candidate agent, a pyruvate oxidase from *Lactobacillus plantarum*, a phosphate ion cofactor and an enzyme that utilizes ADP, under conditions in which, in the absence of the candidate agent, the target protein can produce ADP. The activity of the enzyme in the sample is determined at multiple time points as part of a kinetic assay to determine the activity of the target protein. A change in the activity of the enzyme in the presence of the candidate agent relative to the activity of the enzyme in the absence of the candidate agent is an indication that the candidate agent is a modulator of the target protein.

In some methods, the activity of the enzyme is determined by detecting the formation of a detectable compound that is formed in a coupled enzyme system. The coupled enzyme system can include, for example, one in which the utilization of ADP by the enzyme results in the formation of pyruvate, and the pyruvate oxidase with the phosphate ion cofactor catalyzes a reaction in which pyruvate is oxidized to acetyl phosphate, which reaction is coupled to the formation of the detectable compound.

In another approach, a candidate agent is screened to determine if it is a modulator of the activity of a target protein that can produce guanosine diphosphate (GDP). Some of these methods include preparing a sample that comprises the target protein, a candidate agent and an enzyme that utilizes GDP under conditions in which, in the absence of the candidate agent, the target protein can produce GDP. The activity of the enzyme in the sample is assayed to determine the activity of the target protein.

In some methods, the activity of the enzyme is determined by detecting the formation of a detectable compound that is formed in a coupled enzyme system. The coupled enzyme system can include a reaction in which the utilization of GDP by the enzyme results in the formation of pyruvate, and involve coupling the oxidation of pyruvate that is formed to the formation of the detectable compound. A change in the activity of the enzyme in the presence of the candidate agent relative to the activity of the enzyme in the absence of the candidate agent is an indication that the candidate agent is a modulator of the target protein.

In some methods, the sample can be prepared, for example, by combining the target protein, the candidate agent and the enzyme with phosphoenolpyruvate (PEP), pyruvate kinase (PK), pyruvate oxidase, phosphate and a peroxidase. The coupled enzyme system can involve pyruvate kinase catalyzing the reaction between PEP and GDP formed by the target protein to form pyruvate and GTP, respectively; pyruvate oxidase in the presence of phosphate catalyzing the oxidation of pyruvate to acetylphosphate and the concomitant reduction of oxygen to hydrogen peroxide; the peroxidase catalyzing the oxidation of hydrogen peroxide to superoxide; and the concomitant reaction of the superoxide with the compound to form the detectable compound The activity can be determined in the form of a kinetic assay in which the activity of the enzyme is determined at multiple time points.

In some methods, a plurality of samples is prepared, each sample containing the target protein and one or more of the plurality of candidate agents. The activity of the enzyme is determined for each of the plurality of samples.

The target can generate an initial product that regulates the production of GDP by another protein. The target protein also can generate a substrate for an enzyme that in turn produces GDP. The target protein also can be an activator of a GTPase.

In another approach, methods are provided for screening a candidate agent to determine if it is a modulator of the activity of a target protein that can produce or consume guanosine diphosphate (GDP). Some of these methods involve preparing a sample that includes a target protein, a candidate agent and an enzyme that utilizes GDP under conditions in which, in the absence of candidate agent, the target protein can produce GDP. The activity of enzyme in the sample is determined to determine the activity of the target protein. A change in the activity of the enzyme in the presence of the candidate agent relative to the activity of the enzyme in the absence of the candidate agent is an indication that the candidate agent is a modulator of the target protein.

Some of these methods involve determining the activity of the enzyme by detecting the formation of a detectable compound that has an extinction coefficient of at least 50,000 $M^{-1}cm^{-1}$ and is formed in a coupled enzyme system in which the utilization of GDP by the enzyme is coupled to formation of the detectable compound. The coupled enzyme system can include, for example, a kinase that catalyzes a reaction between GDP and a phosphorylated substrate to form GTP and a dephosphorylated substrate, respectively, and involve coupling the oxidation of the dephosphorylated substrate to the formation of the detectable compound.

In another approach, methods are provided for screening a candidate agent to determine if it is a modulator of the activity of a target protein that can produce guanosine diphosphate (GDP). Some of these methods involve preparing a sample that includes a target protein, a candidate agent, a pyruvate oxidase from *Lactobacillus plantarum*, a phosphate ion cofactor and an enzyme that utilizes ADP, under conditions in which, in the absence of the candidate agent, the target protein can produce GDP. The activity of the enzyme in the sample is determined at multiple time points as part of a kinetic assay to determine the activity of the target protein. A change in the activity of the enzyme in the presence of the candidate agent relative to the activity of the enzyme in the absence of the candidate agent is an indication that the candidate agent is a modulator of the target protein.

In some methods, the activity of the enzyme is determined by detecting the formation of a detectable compound that is formed in a coupled enzyme system in which the utilization of GDP by the enzyme results in the formation of pyruvate, and the pyruvate oxidase with the phosphate ion cofactor catalyzes a reaction in which pyruvate is oxidized to acetyl phosphate, which reaction is coupled to the formation of the detectable compound.

In another embodiment provided herein is a method for identifying whether any two target proteins interact. The method comprises providing a first target chimera comprising a functional molecular motor binding domain and a first target protein. The method further comprises providing a second target chimera comprising a functional microtubule stimulated ATPase domain and a second target protein. Additionally, the method comprises combining the first and second target chimeras under conditions which normally allow activity of a motor protein which comprises a molecular motor binding domain and a microtubule stimulated ATPase domain, wherein an increase in motor protein activity indicates interaction between the two target proteins.

In a further embodiment a method is provided for identifying whether a candidate agent is a modulator of at least one of any two target proteins. The method comprises providing a first target chimera comprising a functional molecular motor binding domain and a first target protein and further providing a second target chimera comprising a functional microtubule stimulated ATPase domain and a second target protein. Additionally, the method comprises combining the first and second target chimeras in the presence and absence of a candidate, wherein a change in motor protein activity, which requires both a molecular motor binding domain and a microtubule stimulated ATPase, between the presence and absence of a candidate agent indicates the candidate agent is a modulator of at least one of the target proteins.

DETAILED DESCRIPTION

I. Definitions

Figure 1:
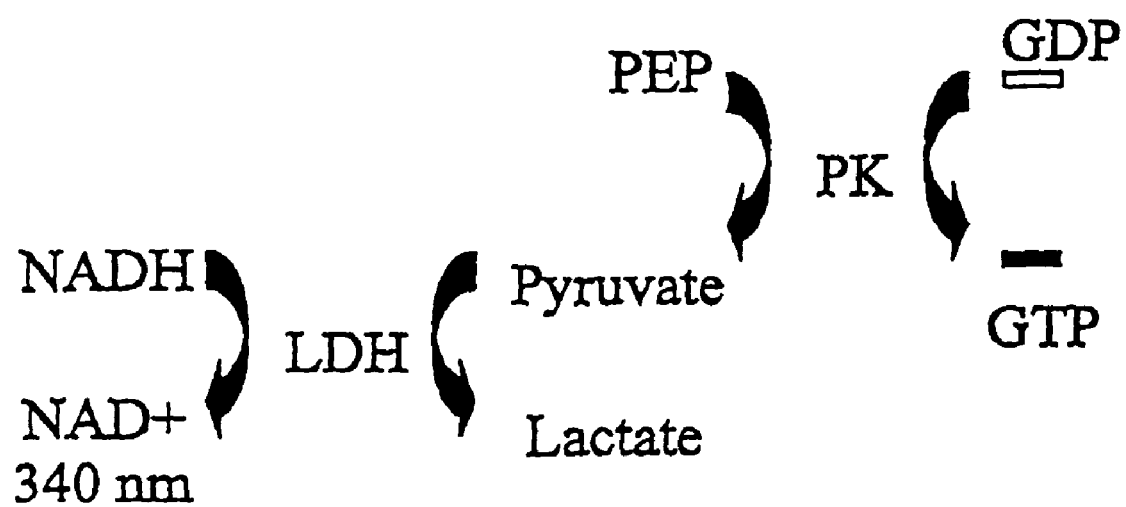
FIG. 1 shows one example of an enzyme coupled assay system that can be utilized to assay for the production of GDP by a target protein that directly or indirectly produces GDP. The assay can be utilized in screening methods to identify modulators of the target protein by conducting the assay, for example, in the presence and absence of a candidate agent. This particular system utilizes pyruvate kinase (PK) to regenerate GTP.

The term "target protein" as used herein refers to a protein that directly or indirectly produces ADP, GDP or phosphate. The target proteins can be from eukaryotes or prokaryotes, including mammals, fungi, bacteria, insects, and plants, as well as viruses. In some embodiments, the target proteins are from mammalian cells, with rodents (mice, rats, hamsters, guinea pigs and gerbils being preferred), primates and humans being preferred, and humans being particularly preferred.

Suitable target proteins, include, but are not limited to ATPases, GTPases, and cytoskeletal proteins including, but not limited to, kinesins, myosins, tubulins, actins, tropomyosins, and troponins, with human proteins being preferred.

The term "protein" means a compound that comprises at least two covalently attached amino acids and includes proteins, polypeptides, oligopeptides and peptides. The proteins may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In some embodiments, the amino acids are in the (S) or L-configuration. If non-naturally occurring side chains are used, non-amino acid substituents may be used, for example to prevent or retard in vivo degradation.

A "control value" or simply "control" generally refers to a value (or range of values) against which an experimental or determined value is compared. Thus, in the case of a screening assay, the control value can be a value for a control reaction that is conducted under conditions that are identical to those of a test assay, except that the control reaction is conducted in the absence of a candidate agent whereas the test assay is conducted in the presence of the candidate agent. The control value can also be a statistical value (e.g., an average or mean) determined for a plurality of control assays. The control assay(s) upon which the baseline value is determined can be conducted contemporaneously with the test or experimental assay or can be performed prior to the test assay. Thus, the baseline value can be based upon contemporaneous or historical controls.

A difference between an experimental and control value can be considered to be "significant" or "statistically significant" if the difference is greater than the experimental error associated with the assay, for example. A difference can also be statistically significant if the probability of the observed difference occurring by chance (the p-value) is less than some predetermined level. As used herein a "statistically significant difference" refers, for example, to a p-value that is <0.05, preferably <0.01 and most preferably <0.001.

II. Overview

The present invention provides assays for detecting ADP, GDP and inorganic phosphate. These assays can be used directly to detect the presence of ADP, GDP and inorganic phosphate or can be used as part of a number of methods for identifying candidate agents that bind to a target protein or serve as modulators of the biological activity of a target protein. Accordingly, the present invention provides, for example, methods of screening candidate agents to identify modulators of target proteins. These assays utilize various methods to measure, in ways amenable to high throughput screening, the generation or consumption of ADP, GDP, or phosphate. That is, target proteins that either directly or indirectly produce or consume ADP, GDP, or phosphate can be screened using the methods that are disclosed herein. By providing assay systems that rapidly, efficiently and inexpensively assay ADP, GDP, or phosphate, modulators (including both antagonists and agonists) of any test protein that directly or indirectly produces ADP, GDP, or phosphate may be found. The present invention thus utilizes high throughput assays that obviate the traditional cumbersome steps of using gels or radioactive materials.

III. Exemplary Target Proteins

A. Target Proteins that Produce or Consume ADP

In some embodiments, the target protein directly or indirectly produces ADP and/or phosphate. Included in the definition of adenosine diphosphate (ADP) are ADP analogs, including, but not limited to, deoxyadenosine diphosphate (dADP) and adenosine analogs. As used herein, phosphate is used interchangeably with inorganic phosphate.

The target protein in some assays directly produces ADP or phosphate. In some assays of this type, the target protein is thus an enzyme having activity that produces ADP and/or phosphate as a reaction product. For example, proteins which directly produce ADP include, but are not limited to, ATPases, kinases, phosphatases and phosphorylases. Suitable ATPases include, but are not limited to, myosins, kinesins, dyneins, DNA gyrase, DNA helicase, topoisomerase I and II, Na+-K+ ATPase, Ca2+ ATPase, F1 subunit of ATP synthase, terminase/DNA packaging protein, recA, heat shock proteins, NSF, katanin, SecA, 5-lipoxygenase, and actin. Suitable kinases include, but are not limited to, tyrosine kinases; serine-threonine kinases; receptor tyrosine kinases; growth factor receptors, including but not limited to, insulin receptor, epidermal growth factor receptor, platelet derived growth factor receptor and fibroblast growth factor receptor; ErbB2; calmodulin dependent protein kinases; protein kinase A; protein kinase C; myosin light chain kinase; CDK2 kinase; ROCK1 kinases; Src kinases; phosphorylase kinase; CheA; adenylate kinase; glycolytic kinases; EIF-2 alpha protein kinases; and Ab1. Suitable phosphatases include, but are not limited to, protein phosphatases, myosin phosphatase, IP3 phosphatase, pyrophosphatase, and Cdc25. Suitable phosphorylases include, but are not limited to, polynucleotide phosphorylase and glycogen phosphorylase.

An "ATPase" as used herein refers to an enzyme that hydrolyzes ATP. For example, ATPases include proteins comprising molecular motors such as kinesins, myosins and dyneins. A "molecular motor" is a molecule that utilizes chemical energy to produce mechanical force or movement; molecular motors are particularly of interest in cytoskeletal systems. For further review, see, Vale and Kreis, 1993, Guidebook to the Cytoskeletal and Motor Proteins, New York: Oxford University Press; Goldstein, 1993, Ann. Rev. Genetics 27: 319-351; Mooseker and Cheney, 1995, Annu. Rev. Cell Biol. 11: 633-675; Burridge et al., 1996, Ann. Rev. Cell Dev. Biol. 12: 463-519.

In certain embodiments, the target protein is a kinesin, including mitotic kinesins. Mitotic kinesins are enzymes essential for assembly and function of the mitotic spindle, but are not generally part of other microtubule structures, such as nerve processes. Mitotic kinesins play essential roles during all phases of mitosis. These enzymes are "molecular motors" that translate energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest. From both the biological and enzymatic perspectives, these enzymes are attractive targets for the discovery and development of novel anti-mitotic chemotherapeutics.

Examples of kinesins that can be assayed include, but are not limited to, Kin2, chromokinesin, Kif1A, KSP, CENP-E, MCAK, HSET, RabK6, Kip3D, Kif15, K335, Q475, D679, FL1, P166, H195, FL2, E433, R494, E658, L360, K491, S553, M329, T340, S405, V465, T488, M1, M2, M3, M4, M5, M6, FL3, A2N370, A2M511, K519, E152.2 Q151.2, Q353, M472 and MKLP1. It is understood that unless a particular species is named, the term "kinesin" includes homologs thereof which may have different nomenclature among species. For example, the human homolog of Kif1A is termed ATSV, the human homologue of Xenopus Eg5 is termed KSP, and human HSET corresponds to Chinese hamster CHO2.

By "kinesin protein activity" or grammatical equivalents herein is meant one of the biological activities of a kinesin protein, including, but not limited to, its ability to affect ATP hydrolysis. Other activities include microtubule binding, gliding, polymerization/depolymerization (effects on microtubule dynamics), binding to other proteins of the spindle, binding to proteins involved in cell-cycle control, or serving as a substrate to other enzymes, such as kinases or proteases and specific kinesin cellular activities such as chromosome congregation, axonal transport, etc.

Methods of performing motility assays are well known to those of skill in the art (see, e.g., Hall et al., 1996, Biophys. J. 71: 3467-3476, Turner et al., 1996, Anal. Biochem. 242 (1): 20-5; Gittes et al., 1996, Biophys. J. 70(1): 418-29; Shirakawa et al., 1995, J. Exp. Biol. 198: 1809-15; Winkelmann et al., 1995, Biophys. J. 68: 2444-53; Winkelmann et al., 1995, Biophys. J. 68: 72S, and the like).

In other embodiments, the target protein indirectly produces ADP or phosphate. In one aspect, a target protein indirectly produces ADP or phosphate by producing a product that then serves as a substrate in a subsequent enzymatic reaction for producing ADP or phosphate. For example, in some embodiments, the target protein can be a pyrophosphate producing enzyme. Suitable pyrophosphate producing enzymes include, but are not limited to, DNA polymerases; RNA polymerases; reverse transcriptase; DNA ligase; adenylate cyclase; guanylate cyclase; PRPP synthetase; tRNA synthetases; acyl CoA synthetase and acetyl CoA carboxylase. Similarly, some ATPases produce AMP that can then be used to make ADP.

In another embodiment, the target protein is a synthase. Thus, substrates for producing phosphate include pyrophosphate and any of the mono-, di- and triphosphate versions of CTP, UTP, GTP, ATP, and TTP, as well as derivatives including dideoxy derivatives. Additionally, other sources of substrates that can be cleaved to phosphate include phosphorylated peptides, oligonucleotides, carbohydrates, lipids, etc. For example, inositol triphosphate (IP3) is an important signaling moiety. Accordingly, any target protein which produces these compounds or others that can be used to produce phosphate or ADP may be assayed using the methods of the present invention.

In another aspect, a target protein indirectly produces ADP or phosphate by regulating an enzyme which produces phosphate or ADP. For example, the target can be an activator of an ATPase, such as an actin filament or a microtubule; thus in this embodiment, the target protein may be a protein polymer or oligomer. Alternatively, the target protein can be a filament binding protein or regulatory protein. For example, the regulatory protein can be the troponin-tropomyosin complex which regulates the binding of myosin to actin. Since myosin's ATPase is activated by binding to actin, modulators of this regulatory protein complex can be identified by the methods provided herein.

In some embodiments, the target protein may consume ADP or phosphate; that is, rather than looking for an increase in signal, a loss of signal may be monitored.

B. Target Proteins that Produce or Consume GDP

Some assays utilize target proteins that directly or indirectly produce GDP and/or phosphate. As used herein, the term "GDP" includes GDP analogs such as deoxyguanine diphosphate (dGDP) and GDP analogs containing analogs of guanosine.

Examples of target proteins that directly produce GDP are ones such as GTPases with a catalytic activity that catalyzes the formation of GDP and/or phosphate. The term "GTPase" refers to a protein that hydrolyzes GTP. Examples of GTPases include, but are not limited to, G proteins; the Rho family GTPases: cdc42, RalA, RhoA and Rac1; Ras proteins; elongation factors including EF1α, EF1βγ, EF-Tu and EF-G; septins; tubulin; ARF related GTPase; rab; SSRP receptor; ATP sulfurylase; rhodopsin; transducin; GTPase activating protein (GAP); cell division protein filamentation temperature-sensitive protein Z (FtsZ); and the cytoskeletal protein tubulin. Other proteins besides GTPases that produce GDP include, for instance, GMP kinase and GDP-mannosyl transferase.

In other instances, the target protein is one that indirectly produces GDP and/or phosphate. Some target proteins of this type are ones that generate a product that subsequently serves as a substrate for another enzyme that ultimately produces GDP or phosphate. Exemplary proteins of this type include, but are not limited to, guanyl phosphoribosyl transferase that produces GMP from guanine nucleoside and ribose phosphate which can then be further phosphorylated by a variety of enzymes such as GMP kinase, to generate GDP.

Another class of target proteins that indirectly produce GDP or phosphate are regulatory proteins that control an enzyme that acts on a substrate to produce GDP or phosphate. Examples of such proteins include guanidine nucleotide exchange factors (GEF's) that activate small GTP binding (G) proteins to release bound GDP.

Whereas some target proteins directly or indirectly produce GDP, other target proteins consume GDP. In assays conducted with such proteins, typically a loss of signal rather than an increase in signal is monitored.

C. Variants

Also included within the definition of the target proteins of the present invention are amino acid sequence variants of wild-type target proteins. These variants fall into one or more of three classes: substitutional, insertional or deletional variants. As for the target proteins as discussed below, these variants ordinarily are prepared by site-specific mutagenesis of nucleotides in the DNA encoding the target protein, using cassette or PCR mutagenesis or other techniques well known in the art, to produce DNA encoding the variant, and thereafter expressing the DNA in recombinant cell culture. However, variant target protein fragments having up to about 100-150 residues can be prepared by in vitro synthesis using established techniques. Amino acid sequence variants are characterized by the predetermined nature of the variation, a feature that sets them apart from naturally occurring allelic or interspecies variation of the target protein amino acid sequence. The variants typically exhibit the same qualitative biological activity as the naturally occurring analogue, although variants can also be selected which have modified characteristics, as discussed more fully below.

While the site or region for introducing an amino acid sequence variation is predetermined, the mutation per se need not be predetermined. For example, in order to optimize the performance of a mutation at a given site, random mutagenesis may be conducted at the target codon or region and the expressed variants screened for the optimal combination of desired activity. Techniques for making substitution mutations at predetermined sites in DNA having a known sequence are well known, for example, M13 primer mutagenesis and PCR mutagenesis. Screening of the mutants is done using assays of target protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the target protein are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trn | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example: the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The variants typically exhibit the same qualitative biological activity, although variants also are selected to modify the characteristics of the target proteins as needed. Alternatively, the variant may be designed such that the biological activity of the target protein is altered. For example, glycosylation sites may be altered or removed.

Further included within the definition of the target proteins of the invention are covalent modifications of the target proteins. One type of covalent modification includes reacting targeted amino acid residues of a target protein with an organic derivatizing agent that is capable of reacting with selected side chains or the N— or C-terminal residues of a target protein. Derivatization with bifunctional agents is useful, for instance, for crosslinking the target protein to a water-insoluble support matrix or surface. Commonly used crosslinking agents include, e.g., 1,1-bis(diazoacetyl)-2-phenylethane, glutaraldehyde, N-hydroxy-succinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification of the target proteins included within the scope of this invention comprises altering the native glycosylation pattern of the polypeptide. "Altering the native glycosylation pattern" is intended for purposes herein to mean deleting one or more carbohydrate moieties found in the target native sequence, and/or adding one or more glycosylation sites that are not present in the native sequence.

Addition of glycosylation sites to target polypeptides may be accomplished by altering the amino acid sequence thereof. The alteration may be made, for example, by the addition of, or substitution by, one or more serine or threonine residues to the native sequence (for O-linked glycosylation sites). The target amino acid sequence may optionally be altered through changes at the DNA level, particularly by mutating the DNA encoding the target polypeptide at preselected bases such that codons are generated that will translate into the desired amino acids.

Another means of increasing the number of carbohydrate moieties on the target polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties present on the target polypeptide may be accomplished chemically or enzymatically or by mutational substitution of codons encoding for amino acid residues that serve as targets for glycosylation. Chemical deglycosylation techniques are known in the art and described, for instance, by Hakimuddin et al., Arch. Biochem. Biophys. 259:52 (1987) and by Edge et al., Anal. Biochem. 118:131 (1981). Enzymatic cleavage of carbohydrate moieties on polypeptides can be achieved by the use of a variety of endo- and exo-glycosidases as described by Thotakura et al., Meth. Enzymol. 138:350 (1987).

Another type of covalent modification of target proteins comprises linking the target polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Target polypeptides of the present invention may also be modified in a way to form chimeric molecules comprising a target protein fused to another, heterologous polypeptide or amino acid sequence, which is described more fully below. In one embodiment, such a chimeric molecule comprises a fusion of a target polypeptide with a tag polypeptide which provides an epitope to which an anti-tag antibody can selectively bind. The epitope tag is generally placed at the amino- or carboxyl-terminus of the target polypeptide. The presence of such epitope-tagged forms of a target polypeptide can be detected using an antibody against the tag polypeptide. Also, provision of the epitope tag enables the target polypeptide to be readily purified by affinity purification using an anti-tag antibody or another type of affinity matrix that binds to the epitope tag.

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., Mol. Cell. Biol. 8:2159-2165 (1988)); the c-myc tag and the 8F9, 3C7, 6E10, G4, B7 and 9E10 antibodies thereto (Evan et al., Molecular and Cellular Biology 5:3610-3616 (1985)); and the Herpes Simplex virus glycoprotein D (gD) tag and its antibody (Paborsky et al., Protein Engineering 3(6):547-553 (1990)). Other tag polypeptides include the Flag-peptide (Hopp et al., BioTechnology 6:1204-1210 (1988)); the KT3 epitope peptide (Martin et al., Science 255:192-194 (1992)); tubulin epitope peptide (Skinner et al., J. Biol. Chem. 266:15163-15166 (1991)); and the T7 gene 10 protein peptide tag (Lutz-Freyemuth et al., Proc. Natl. Acad. Sci. USA 87:6393-6397 (1990)).

As will be appreciated by those in the art, the target proteins can be made in a variety of ways, including both synthesis de novo and by expressing a nucleic acid encoding the target protein.

Numerous suitable methods for recombinant protein expression, including generation of expression vectors, generation of fusion proteins, introducing expression vectors into host cells, protein expression in host cells, and purification methods are known to those in the art and are described, for example, in the following textbooks: Sambrook et al., Molecular Cloning: A Laboratory Manual (New York: Cold Spring Harbor Laboratory Press, 1989); Ausubel et al., Short Protocols in Molecular Biology (John Wiley & Sons, Inc., 1995); Harlow and Lane, Antibodies: A Laboratory Manual (New York: Cold Spring Harbor Laboratory Press, 1988); O'Reilly et al., Baculovirus Expression Vectors: A Laboratory Manual (New York: Oxford University Press, 1994); Richardson, Baculovirus Expression Protocols (Totowa: Humana Press, 1995); Kriegler, Gene Transfer and Expression: A Laboratory Manual (New York: Oxford University Press, 1991); Roth, Protein Expression in Animal Cells, Methods in Cell Biology Vol. 43 (San Diego: Academic Press, 1994); Murray, Gene Transfer and Expression Protocols, Methods in Molecular Biology, Vol 7 (Clifton: Humana Press, 1991); Deutscher, Guide to Protein Purification, Methods in Enzymology Vol. 182 (San Diego: Academic Press, Inc., 1990); Harris and Angal, Protein Purification Methods: A Practical Approach (Oxford: IRL Press at Oxford University Press, 1994); Harris and Angal, Protein Purification Applications: A Practical Approach (Oxford: IRL Press at Oxford University Press, 1990); Rees et al., Protein Engineering, A Practical Approach (Oxford: IRL Press at Oxford University Press, 1992); and White, PCR Protocols, Methods in Molecular Biology, Vol. 15 (Totowa, Humana Press, 1993).

The selection of host cell types for the expression of target proteins will depend on the target protein, with both eukaryotic and prokaryotic cells finding use in the invention. Appropriate host cells include yeast, bacteria, archaebacteria, fungi, plant, insect and animal cells, including mammalian cells. Of particular interest are *Drosophila melanogaster* cells, *Saccharomyces cerevisiae* and other yeasts, *E. coli, Bacillus subtilis*, SF9 cells (and other related cells for use with baculoviral expression systems); C129 cells, 293 cells, Neurospora, BHK, CHO, COS, Dictyostelium, etc.

In some embodiments, the target proteins are purified for use in the assays, as outlined herein, to provide substantially pure samples. The terms "substantially pure" or "isolate" as used herein mean that the protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. Alternatively, the target protein need not be substantially pure as long as the sample comprising the target protein is substantially free of other components that can contribute to the production of GDP, ADP or phosphate (or, in the case of indirect assays, other components which are subsequently assayed).

The target proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, reverse-phase HPLC chromatography, and chromatofocusing. For example, the target protein may be purified using a standard anti-target antibody column. Ultrafiltration and diafiltration techniques, in conjunction with protein concentration, are also useful. For general guidance in suitable purification techniques, see Scopes, R., Protein Purification, Springer-Verlag, N.Y. (1982).

Suitable purification schemes for some specific kinesins are outlined in U.S. Ser. No. 09/295,612, filed Apr. 20, 1999, hereby expressly incorporated herein in its entirety, along with referenced materials.

IV. Assay Methods and Screening Methods

A. General

A number of assay method are described herein that can be utilized to detect the presence of ADP, GDP and inorganic phosphate (see, e.g., FIGS. 1-4). These assays are described herein primarily in the context of their utility in screening methods to identify candidate agents that modulate the activity of target proteins that either produce or consume ADP, GDP or inorganic phosphate. It should also be appreciated, however, that these assays can be used independently to assay for the presence of GDP, ADP or inorganic phosphate. The assays thus are useful in a wide variety of methods in which detection of ADP, GDP, or inorganic phosphate is desired.

A number of the methods provided herein utilize the assays to screen for modulators of target proteins. By "modulators"

herein is meant both antagonists and agonists of the target protein. Thus, "modulating the activity of the target protein" includes an increase in target protein activity, a decrease in target protein activity, or a change in the type or kind of activity present. Generally, the modulator will both bind to the target protein (although this may not be necessary), and alter its biological or biochemical activity as defined herein. For inhibitors, changes of 25%, 50%, 75% and most preferably 100% of at least one biological activity of the target protein is seen. For activators, preferably the change is a change of at least 40%, more preferably at least 60%, more preferably at least 80%, more preferably at least 100%, more preferably at least 200%, and most preferably by at least 500%.

In certain embodiments, the methods involve combining a target protein and a candidate bioactive agent, and evaluating the effect on the target protein's activity. By "target protein activity" or grammatical equivalents herein is meant a biological activity of the target protein. As will be appreciated by those in the art, the activity of the target protein will vary with the target protein chosen, and will be ascertainable by one of skill in the art of the target protein.

Some methods of the invention involve the addition of candidate agents to a target protein, in which the target protein directly or indirectly produces ADP, GDP, or inorganic phosphate. In general, such additions are done under conditions which normally allow the direct or indirect production of ADP, GDP or phosphate by the target protein. The phrase "under conditions which normally allow production or utilization of ADP, GDP, or phosphate" as used herein means that all of the compositions and conditions are provided to allow the production or utilization of ADP, GDP or phosphate. Thus, the reaction which directly or indirectly produces or uses ADP, GDP, or phosphate would normally occur in the absence of the modulator.

A modulator of a target protein which directly or indirectly produces or uses ADP, GDP, or phosphate can be any compound as described herein in the context of candidate agents (see below) which modulates the target protein's direct or indirect production or use of ADP, GDP or phosphate relative to a control.

Some screening methods that are provided utilize an enzymatic reaction that uses ADP, GDP or phosphate as a substrate to detect the formation of ADP, GDP or inorganic phosphate by the target protein and thus the level of activity of the enzymatic reaction. These reactions are conducted under conditions which normally allow the ADP, GDP or phosphate to be utilized. Such enzymatic reactions can be performed in conjunction with identifying a modulator of a target protein which directly or indirectly produces ADP, GDP, or phosphate. Alternatively, certain assays can be used to identify a protein that uses ADP, GDP, or phosphate.

The phrase to "use ADP or phosphate" as used herein means that the ADP or phosphate are directly acted upon. In one case, the ADP, for example, can be hydrolyzed or can be phosphorylated or depurinated. As another example, the phosphate can be added to another compound. As used herein, in each of these cases, ADP or phosphate is acting as a substrate.

Similarly, the phrase to "use GDP or phosphate" means that GDP or phosphate are directly acted upon. GDP, for instance, can be hydrolyzed, depurinated, phosphorylated or a phosphate group transferred to another compound. Each of these examples illustrates a situation in which GDP is acting as a substrate.

Sometimes the activity of the target protein in the presence of the candidate agent is compared with a control value (control), such as the activity of target protein in a parallel reaction that is conducted in the absence of the candidate agent but otherwise is conducted under the same conditions as the reaction with the candidate agent. As noted above, however, a control reaction does not necessarily need to be conducted contemporaneously with the test reaction. A comparison, for instance, can be based upon values (e.g., an average value) determined previously (i.e., historical control data).

Regardless of the specific nature of the control, a change (e.g., one that is "statistically significant") in the target protein activity in the presence of the candidate agent relative to the activity in the absence of the candidate agent indicates that the candidate agent is a modulator of the target protein. More specifically, a decrease in activity in the presence of the candidate agent indicates that it is an inhibitor or antagonist of the target protein; whereas, an increase in activity indicates the candidate agent is an agonist of the target protein.

Some screening methods that are provided are in vitro methods, utilizing purified or partially purified target proteins. Other methods that are provided are in vivo methods, utilizing cells comprising target nucleic acids that can be expressed to produce target proteins, particularly when the target protein is either secreted or expressed on the cell surface.

As will be appreciated by those in the art, the components are added in buffers and reagents to assay target protein activity and give optimal signals (i.e., the largest ADP, GDP or phosphate signals possible). Since the methods outlined herein allow kinetic measurements, the incubation periods are optimized to give adequate detection signals over the background.

In some embodiments, detection of the assay is done using a detectable label. By "labeled" herein is meant that a compound has at least one element, isotope or chemical compound attached to enable the detection of the compound. In general, labels fall into three classes: a) isotopic labels, which may be radioactive or heavy isotopes; b) magnetic, electrical, thermal; and c) colored or luminescent dyes; although labels include enzymes and particles such as magnetic particles as well. The dyes may be chromophores or phosphors but are preferably fluorescent dyes, which due to their strong signals provide a good signal-to-noise ratio for detection. Suitable dyes for use in the invention include, but are not limited to, fluorescent lanthanide complexes, including those of Europium and Terbium, fluorescein, rhodamine, tetramethyirhodamine, eosin, erythrosin, coumarin, methyl-coumarins, pyrene, Malachite green, stilbene, Lucifer Yellow, Cascade™, Texas Red, and derivatives thereof, and others described in the 6th Edition of the Molecular Probes Handbook by Richard P. Haugland, hereby expressly incorporated by reference.

In some embodiments, an antifoam or a surfactant is included in the assay mixture and wash solution. Suitable antifoams include, but are not limited to, antifoam 289 (Sigma), and others commercially available. Suitable surfactants include, but are not limited to, Tween, Tritons including Triton X-100, saponins, and polyoxyethylene ethers. This eliminates bubbles which often result in conventional methods requiring pipetting into low volume assay wells. Thus, in some embodiments, the invention includes the use of an antifoam, detergent or surfactant as a reagent in a high throughput screens, including, but not limited to the screens of the invention. Generally the antifoams, detergents or surfactants are added at a range from about 0.01 ppm to about 10 ppm, with from about 1 to about 2 ppm being preferred. In a further embodiment, the invention includes the use of an antifoam, surfactant or detergent when the assay requires mixing, particularly physical mixing such as shaking the microtiter plates. In an additional embodiment, the invention includes the use of an antifoam, surfactant or detergent when the assay is done in microtiter plates, particularly plates with 96 wells or more, including 96, 384 and 1536 plates.

In another aspect, a round sample well is used. This helps increase the path length for absorbance measurements for a given assay volume and helps flatten the meniscus of the solution in each assay well. But in some assays sample wells of other shapes are utilized, such as those with a square, trapezoidal or conical shape. The methods typically involve vigorous shaking of the sample plate following the addition of each reagent.

In one embodiment, the methods comprise automated liquid handling. Some methods, for example, utilize robotic systems to transfer and combine assay components.

B. Candidate Agents

By "candidate agent" or "candidate bioactive agent" or "drug candidate" or grammatical equivalents herein is meant any molecule, e.g., protein, oligopeptide, small organic molecule, polysaccharide, or polynucleotide, to be tested in a screening assay.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines (including derivatives, structural analogs, or combinations thereof), derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In an embodiment provided herein, the candidate bioactive agents are proteins. The protein may be made up of naturally occurring amino acids and peptide bonds, or synthetic peptidomimetic structures. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In some embodiments, the amino acids are in the (S) or L-configuration. If non-naturally occurring side chains are used, non-amino acid substituents may be used, for example to prevent or retard in vivo degradations.

In another embodiment, the candidate bioactive agents are naturally occurring proteins or fragments of naturally occurring proteins. Thus, for example, cellular extracts containing proteins, or random or directed digests of proteinaceous cellular extracts, may be used. In one embodiment, the libraries are of bacterial, fungal, viral, and mammalian proteins, with the latter being preferred, and human proteins being especially preferred.

In one embodiment, the candidate agents are peptides of from about 2 to about 30 amino acids, with from about 5 to about 20 amino acids being preferred, and from about 7 to about being particularly preferred. The peptides may be digests of naturally occurring proteins as is outlined above, or random peptides. By randomized or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In some embodiments, the library is biased. That is, some positions within the sequence are either held constant, or are selected from a limited number of possibilities. For example, in some embodiments, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In another embodiment, the candidate agents are nucleic acids. By nucleic acid or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al., Chem. Lett. 805 (1984); Letsinger et al., J. Am. Chem. Soc. 110:4470 (1988); and Pauwels et al., Chemica Scripta 26:141 (1986)); phosphorothioate (Mag et al., Nucleic Acids Res. 19:1437 (1991); and U.S. Pat. No. 5,644, 048), phosphorodithioate (Briu et al., J. Am. Chem. Soc. 111:2321 (1989)), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995)); non-ionic backbones (U.S. Pat. Nos. 5,386, 023; 5,637,684; 5,602,240; 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, Carbohydrate Modifications in Antisense Research, Ed. Y. S. Sanghui and P. Dan Cook; Mesmaeker et al., Bioorganic & Medicinal Chem. Lett. 4:395 (1994); Jeffs et al., J. Biomolecular NMR 34:17

(1994); Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carboxylic sugars are also included within the definition of nucleic acids (see Jenkins et al., Chem. Soc. Rev. (1995) pp. 169-176). Several nucleic acid analogs are described in Rawls, C & E News, Jun. 2, 1997, p. 35. All of these references are hereby expressly incorporated by reference. These modifications of the ribose-phosphate backbone may be done to facilitate the addition of additional moieties such as labels, or to increase the stability and half-life of such molecules in physiological environments.

In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo-and ribo-nucleotides, and any combination of bases, including uracil, adenine, thymine, cytosine, guanine, inosine, xanthine, hypoxanthine, isocytosine, isoguanine, etc.

As described above generally for proteins, nucleic acid candidate agents may be naturally occurring nucleic acids, random nucleic acids, or biased random nucleic acids. For example, digests of prokaryotic or eukaryotic genomes may be used as is outlined above for proteins.

In some embodiments, the candidate bioactive agents are organic chemical moieties, a wide variety of which are available in the literature.

In some embodiments, the candidate agent is a small molecule. The small molecule is preferably 4 kiloDaltons (kDa) or less. In another embodiment, the compound is less than 3 kDa, 2 kDa or 1 kDa. In another embodiment the compound is less than 800 daltons (Da), 500 Da, 300 Da or 200 Da. Alternatively, the small molecule is about 75 Da to 100 Da, or alternatively, 100 Da to about 200 Da.

Devices for the preparation of combinatorial libraries are commercially available (see, e.g., 357 MPS, 390 NWS, Advanced Chem Tech, Louisville Ky.; Symphony, Rainin, Woburn, Mass.; 433A Applied Biosystems, Foster City, Calif.; 9050 Plus, Millipore, Bedford, Me.).

It is understood that once a modulator or binding agent is identified that it can be subjected to further assays to further confirm its activity. In particular, the identified agents can be entered into a computer system as lead compounds and compared to others which may have the same activity. The agents may also be subjected to in vitro and preferably in vivo assays to confirm their use in medicine as a therapeutic or diagnostic or in the agricultural arena.

C. High Throughput Screening

The invention provides methods of screening candidate agents for the ability to serve as modulators of target protein activity. In some embodiments, high throughput screening (HTS) systems are used, which can include the use of robotic systems. The assays of the present invention offer the advantage that many samples can be processed in a short period of time. For example, plates having 96, 384, 1536 or as many wells as are commercially available can be used.

High throughput screening systems are commercially available (see, e.g., Zymark Corp., Hopkinton, Mass.; Air Technical Industries, Mentor, Ohio; Beckman Instruments, Inc., Fullerton, Calif.; Precision Systems, Inc., Natick, Mass., etc.) These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems, i.e., Zymark Corp., provide detailed protocols for the various high throughput assays.

Generally a plurality of assay mixtures are run in parallel with different agent concentrations to obtain a differential response to the various concentrations. Typically, one of these concentrations serves as a negative control, i.e., at zero concentration or below the level of detection. However, in some embodiments, any concentration can be used as the control for comparative purposes.

Some high throughput screening methods that are provided involve providing a library containing a large number of compounds (candidate compounds) potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics or agricultural compounds.

For example, in one embodiment, candidate agents are assayed in highly parallel fashion by using multiwell plates by placing the candidate agents either individually in wells or testing them in mixtures. Assay components, such as for example, a target protein (e.g., ATPase, GTPase, molecular motors, protein filaments), coupling enzymes, substrates, and ATP or GTP can then be added to the wells and the absorbance or fluorescence of each well of the plate measured by a plate reader. A candidate agent which modulates the function of the target protein is identified by an increase or decrease in the rate of ATP or GTP hydrolysis compared to a control assay in the absence of that candidate agent.

One exemplary HTS system is as follows. The system comprises a microplate input function which has a storage capacity matching a logical "batch " size determined by reagent consumption rates. The input device stores and, delivers on command, barcoded assay plates containing pre-dispensed samples, to a barcode reader positioned for convenient and rapid recording of the identifying barcode. The plates are stored in a sequential nested stack for maximizing storage density and capacity. The input device can be adjusted by computer control for varying plate dimensions. Following plate barcode reading, the input device can be adjusted by computer control for varying plate dimensions. Following plate barcode reading, the input device transports the plate into the pipetting device which contains the necessary reagents for the assay. Reagents are delivered to the assay plate with the pipetting device. Tip washing in between different reagents is performed to prevent carryover. A time dependent mixing procedure is performed after each reagent to effect a homogeneous solution of sample and reagents. The sequential addition of the reagents is delayed by an appropriate time to maximize reaction kinetics and readout levels. Immediately following the last reagent addition, a robotic manipulator transfers the assay plate into an optical interrogation device which records one or a series of measurements to yield a result which can be correlated to an activity associated with the assay. The timing of the robotic transfer is optimized by minimizing the delay between "last reagent" delivery and transfer to the optical interrogation device. Following the optical interrogation, the robotic manipulator removes the finished assay plates to a waste area and proceeds to transfer the next plate from pipetting device to optical interrogation device. Overlapping procedures of the input device, pipetting device and optical interrogation device are used to maximize throughput.

In one embodiment, approximately 1000 assays are performed per hour with very low false negative and false positive rates, with up to 10,000 assays an hour being preferred and more than 100,000 assays per hour being particularly preferred. In another embodiment, at least one or more of the steps regarding automated liquid handling or preferred assay design as described herein are included.

D. Multi-Time-Point Kinetic Assays

Some assays use a multi-time-point (kinetic) assay, with at least two data points being preferred. As will be appreciated by those in the art, the interval can be adjusted to correlate with the biological activity of the protein. In the case of multiple measurements the absolute rate of the protein activity can be determined, and such measurements have higher specificity particularly in the presence of candidate agents which have similar absorbance or fluorescence properties to that of the enzymatic readout. The kinetic assay reduces the false positive rate. In an additional aspect, the kinetic rates are normalized to several control wells on each assay plate. This allows for some variation in the activity of the target proteins and the stability of assay reagents over time and thus permits screening runs of several hours.

V. Exemplary Assays to Detect ADP Production by Target Proteins

A. Coupled Enzyme Assays to Detect ADP Production Involving NADH

There are, for example, a number of enzymatic reactions known in the art which use ADP as a substrate. For example, kinase reactions such as pyruvate kinases are well known. Greengard, Nature 78:632-634 (1956); Hart, Mol. Pharmacol. 6(1):31-40 (1970). This is a useful method in that it allows the regeneration of ATP, which can then be used by the target protein. In one embodiment, the level of activity of the enzymatic reaction is determined directly. For example, in a pyruvate kinase (PK) reaction, pyruvate or ATP can be measured by conventional methods known in the art.

In some embodiments, the level of activity of the enzymatic reaction which uses ADP as a substrate is measured indirectly by being coupled to another reaction. For example, in one embodiment, the method further comprises a lactate dehydrogenase (LDH) reaction under conditions which normally allow the oxidation of NADH, wherein said lactate dehydrogenase reaction is dependent on the pyruvate kinase reaction. Measurement of enzymatic reactions by coupling is discussed, for example, in Greengard, Nature 178:632-634 (1956) and is further discussed below in regards to fluorescence methods.

It is understood that the methods provided herein can be applied to a varied array of target proteins and are not limited to cytoskeletal component systems. However, for illustrative purposes, an example of the present invention is to assay for modulators of the polymerized state of cytoskeletal filament proteins actin or tubulin. In this example, the candidate agent or mixture comprising at least one candidate agent is incubated with the filament protein under conditions that would normally promote either polymerization or depolymerization. A molecular motor that is activated by the filament is then added to the assay mixture and its activity is monitored by ADP or phosphate release as discussed above. Candidate agents which increase the fraction of the filament protein in a polymerized state will be identified by an increase in the motor ATPase and those which increase the fraction of the filament protein in a depolymerized state will be identified by a decrease in the motor ATPase.

When proteins that use ATP are included, the pyruvate kinase/lactate dehydrogenase embodiments are particularly preferred due to the advantage of ATP regeneration so that ATP concentration is constant over time.

Thus, some screening methods designed to identify candidate agents that modulate the activity of a target protein involve combining a target protein that can directly or indirectly produce ADP with ATP, phosphoenolpyruvate (PEP), pyruvate kinase (PK), lactate dehydrogenase (LDH) and NADH. The added pyruvate kinase catalyzes a reaction between PEP and the ADP produced by the target protein to produce pyruvate and regenerate ATP. LDH then reduces the pyruvate that is formed to lactate, with the concomitant oxidation of NADH to NAD+. Assays are usually conducted in both the presence and absence of the candidate agent to determine if the candidate agent has an affect on the activity of the target protein.

B. Non-NADH Coupled Enzyme Assays to Identify ADP Production

Other assays and screening methods utilize coupled enzyme systems but do not involve detecting the consumption (i.e., oxidation) of NADH. Instead, the coupled enzyme system (in a series of one or more coupled enzyme reactions) couples the utilization of ADP produced by the target protein to the formation of a detectable compound that has a higher extinction coefficient, thereby providing increased sensitivity. The methods can utilize selected dye compounds, for instance, that produce a detectable product (e.g., a fluorescent compound) that has an extinction coefficient of at least 30,000 $M^{-1}cm^{-1}$, 40,000 $M^{-1}cm^{-1}$, 50,000 $M^{-1}cm^{-1}$, or 60,000 $M^{-1}cm^{-1}$, or any range therebetween.

In some methods, the ADP produced by the target enzyme is coupled to the regeneration of ATP and the formation of pyruvate (e.g., in a pyruvate kinase reaction). The oxidation of the pyruvate is coupled in turn to the formation of the detectable product.

An example of this type of assay generally involves combining a target protein and an enzyme that can utilize the ADP produced directly or indirectly by the target protein. In the coupled enzyme system in this particular assay, utilization of ADP by the enzyme is coupled to the conversion of a phosphorylated substrate to a dephosphorylated substrate by the enzyme, thereby resulting in the regeneration of ATP from ADP. Another reaction in the coupled system, the oxidation of the dephosphorylated substrate is coupled to the reduction of an oxidized substrate to form a reduced substrate. Finally, the reduced substrate is oxidized in another enzymatic reaction, with the concomitant reduction of a dye molecule (e.g., fluorophore) to form the detectable compound with the high extinction coefficient. Here, too, screening methods utilizing such assays are generally conducted in the presence and absence of a candidate agent to determine whether the candidate agent affects the activity of the target protein.

Figure 3:
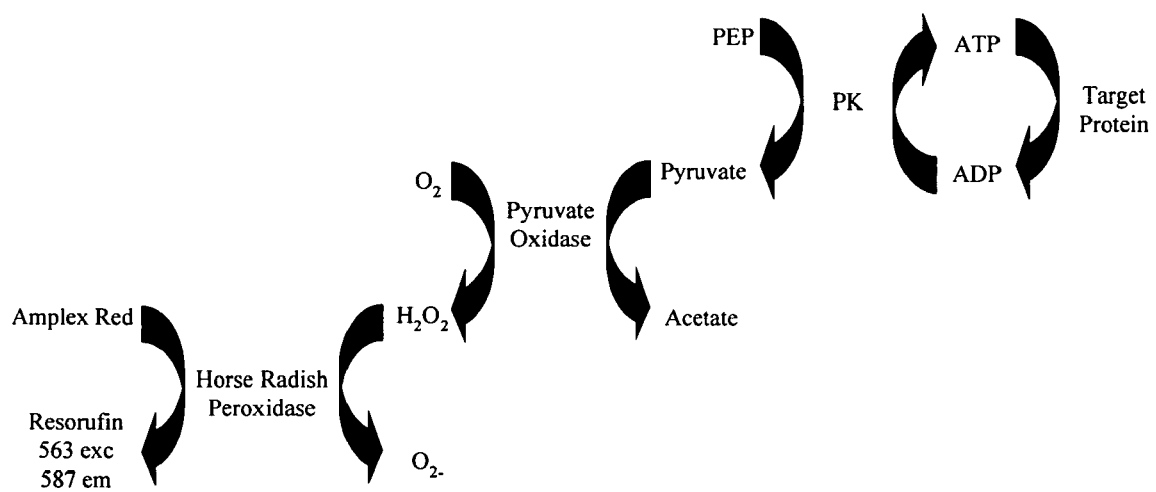
FIG. 3 shows one example of an enzyme coupled assay system that can be utilized to assay for the production of ADP by a target protein that directly or indirectly produces ADP. The assay can be utilized in screening methods to identify modulators of the target protein by conducting the assay, for example, in the presence and absence of a candidate agent. This particular system utilizes pyruvate kinase to regenerate ATP and couples the oxidation of pyruvate to the conversion of AMPLEX RED (Molecular Probes, Inc., Eugene Oreg.) to Resorufin.

FIG. 3 depicts a specific example of this approach. In the particular assay shown in this figure, ATP, pyruvate kinase, PEP, pyruvate oxidase, a peroxidase (e.g., horse radish peroxidase, HRP) and 10-acetyl-3,7-dihydroxyphenoxazine (AMPLEX RED, Molecular Probes, Inc., Eugene, Oreg.) are combined in an assay. ADP produced by the target enzyme is thus coupled to the conversion of PEP to pyruvate through the enzymatic activity of pyruvate kinase; this conversion also results in the regeneration of ATP from ADP. The oxidation of the pyruvate that is formed occurs with the reduction of oxygen to hydrogen peroxide via the enzymatic activity of pyruvate oxidase. The oxidation of the resulting hydrogen peroxide is coupled to the reduction of 10-acetyl-3,7-dihydroxyphenoxazine using horse radish peroxidase to form 3H-phenoxazin-3-one, 7-hydroxy (RESORUFLN, Molecular Probes, Inc., Eugene, Oreg.), which can be excited at a wavelength of 563 nm and emits at a wavelength of 587 nm. The extinction coefficient for 3H-phenoxazin-3-one, 7-hydroxy is 58,000 $M^{-1}$ $cm^{-1}$.

Assays of this general type in which the oxidation pyruvate is coupled to the formation of a detectable product can be conducted with pyruvate oxidases from various sources. Suitable pyruvate oxidases include, for example, E. coli pyruvate oxidase (ICN) and Lactobacillus plantarum (Sigma).

The current inventors have found that use of pyruvate oxidase from Lactobacillus plantarum can give significantly improved sensitivity as compared to pyruvate oxidases from other sources. This particular pyruvate oxidase utilizes phosphate as a cofactor. Assays conducted with this particular enzyme thus also include phosphate (e.g., sodium or potassium phosphate (mono or dibasic) at about 2 mM). In assays conducted with pyruvate oxidases of this type that utilize phosphate as a cofactor, pyruvate oxidase catalyzes the reaction between pyruvate, oxygen and phosphate ion to form acetyl phosphate (rather than simply acetate as is the case with pyruvate oxidases that do not utilize phosphate as a cofactor) and hydrogen peroxide.

Other versions of 10-acetyl-3,7-dihydroxyphenoxazine such as Amplex Deep Red (Molecular Probes), which has approximately twice the extinction coefficient of 10-acetyl-3,7-dihydroxyphenoxazine, can be used for detection in this coupled system.

The assays can be conducted using two mixes that contain the necessary assay components to facilitate high throughput screening. For example, in some assays one mixture includes ATP, PEP, dye (e.g., 10-acetyl-3,7-dihydroxyphenoxazine (AMPLEX RED)) and target protein. The second mixture contains pyruvate kinase, microtubules, pyruvate oxidase and a peroxidase enzyme (e.g., horse radish peroxidase). In certain high throughput screening assays, samples containing one or more candidate agents are placed in sample wells on a multi-well plate. An aliquot from the first mixture is then transferred to each of the sample wells, followed by an aliquot from the second mixture. The resulting mixtures are subsequently mixed and signal (e.g., absorbance or fluorescence) measured at each of the wells.

Assays utilizing dyes with high extinction coefficients can be performed as end point assays, but the increased sensitivity possible with such dyes means that kinetic analyses can also be readily performed. The further increase in sensitivity that can be achieved using the Lactobacillus plantarum/phosphate cofactor combination further enhance the capabilities of conducting the assays in kinetic formats. As noted above, kinetic assays are ones in which measurements are made at multiple time points (e.g., a reading about every 1 minute). Further details regarding such assays are provided in Example 3.

VI. Exemplary Assays to Detect GDP Formation by Target Proteins

A. General

A variety of assays for detecting the production of GDP and/or inorganic phosphate are also provided herein. These assays can be utilized, among other things, to rapidly screen large numbers of compounds to identify those that are modulators of target proteins that directly or indirectly produce or consume GDP and inorganic phosphate. These assays can be conducted in homogeneous formats such that the GDP and/or inorganic phosphate can be detected directly in solution without any purification required prior to detection of these products. The assays can thus also be conducted in real time, with production of GDP and/or inorganic phosphate detected in solution as it is formed over time. Many of the assays can be conducted with reagents, including enzymes that are inexpensive and readily available from a variety of commercial sources. Many assays can thus be conducted at minimal cost.

One class of methods that are provided are those in which the production of GDP and/or inorganic phosphate are detected via an enzymatic assay that utilizes GDP or inorganic phosphate. Another class are based on non-enzymatic detection schemes in which the GDP or inorganic phosphate that is produced is reacted with a reagent that then forms a detectable product whose formation can be detected.

Some screening methods that utilize enzymatic assays generally involve contacting a target protein (e.g., a GTPase) with a candidate agent. The protein and candidate agent are contacted under conditions which normally allow for the production of GDP and inorganic phosphate by the target protein. Thus, the reaction conditions are such that in the absence of the candidate agent the target protein would normally be able to generate GDP or inorganic phosphate. GDP and/or inorganic phosphate produced by the target protein is detected with an assay system that utilizes GDP or inorganic phosphate to determine the activity of the target protein.

B. Coupled Enzyme Assays using NADH to Detect GDP Production

Some of the enzymatic screening methods are conducted with a coupled enzyme assay in which the utilization of GDP is coupled to the production of a detectable product. One general coupled enzyme approach involves coupling the conversion of GDP to GTP to the oxidation of NADH to NAD+. The consumption of NADH in this approach is thus a measure of the amount of GDP produced by the target protein. By monitoring the consumption of NADH with time, one can track the production of GDP and inorganic phosphate in real time.

Certain coupled enzyme systems involve combining a target protein, GTP, the candidate agent, a phosphorylated substrate, a kinase that can utilize the phosphorylated substrate as a substrate, a dehydrogenase, and NADH in solution. The kinase catalyzes the reaction between the phosphorylated substrate and the GDP produced by the target protein to form a dephosphorylated substrate and GTP, respectively. The dehydrogenase enzyme that is present in the assay mixture catalyzes the reaction between the dephosphorylated substrate (as it is formed) with NADH that is present to form a reduced substrate and NAD+, respectively. So the activity of the target protein can be determined from the conversion of NADH to NAD+.

One specific screening method that uses this general approach is shown in FIG. 1. In this particular approach, the target protein is combined with GTP, the candidate agent, pyruvate kinase (the kinase), phosphoenolpyruvate (PEP; the phosphorylated substrate), lactate dehydrogenase (the dehydrogenase enzyme) and NADH. As shown in FIG. 1, the GDP that is formed by target protein is then utilized as a substrate by pyruvate kinase together with PEP to form pyruvate (dephosphorylated substrate) and GTP. Lactate dehydrogenase, using NADH as a co-substrate, catalyzes the reduction of pyruvate to lactate, with the concomitant oxidation of NADH to NAD+. The ability to utilize this particular approach is surprising because pyruvate kinase has a significantly lower affinity for GDP as compared to ADP. Pyruvate kinase is thus most typically thought to be useful in assays of ADP rather than GDP. In general, the concentration of pyruvate kinase in the assays for GDP is higher than in assays for ADP (e.g., 5-10 times higher). Typical, pyruvate kinase concentrations in the GDP assays are about 15-30 U/ml.

Other coupled enzyme systems utilize nucleotide diphosphate kinase (NDPK) to convert GDP produced by the target protein back to GTP. In this approach, NDPK is combined with a nucleotide triphosphate other than GTP (e.g., ATP), a phosphorylated substrate, a second kinase that can utilize the phosphorylated substrate as a substrate, a dehydrogenase and NADH. With this combination of reagents, NPDK catalyzes a reaction between GDP produced by the target protein and the nucleotide triphosphate to regenerate GTP and to form a nucleotide diphosphate corresponding to the added nucleotide triphosphate, respectively. The kinase then catalyzes a phosphoryl transfer reaction between the phosphorylated substrate and the nucleotide diphosphate to yield respectively a dephosphorylated substrate and the nucleotide triphosphate, thereby regenerating the nucleotide triphosphate. Finally, the dehydrogenase enzyme catalyzes the reduction of the dephosphorylated substrate to a reduced substrate, with the concomitant oxidation of NADH to NAD+.

Figure 2:
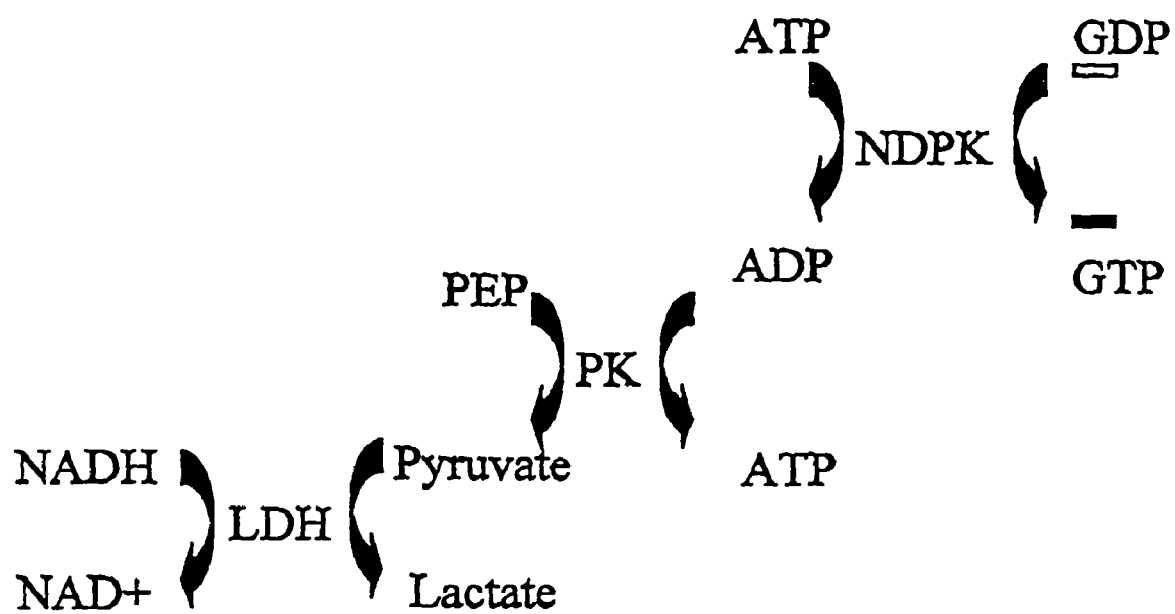
FIG. 2 depicts another exemplary enzyme coupled assay system that can be utilized as part of a screening method to identify modulators of a target protein that directly or indirectly produces GDP. This particular system utilizes nucleotide diphosphate kinase to regenerate GTP.

A specific example of a screening method utilizing this general approach is shown in FIG. 2. In this instance, target protein, candidate agent, NPDK, ATP (the nucleotide triphosphate), PEP (the phosphorylated substrate), pyruvate kinase (PK; the second kinase), lactate dehydrogenase (LDH; the dehydrogenase) and NADH are combined to form an assay solution. In this particular system, the GDP produced by the target protein is reconverted back to GTP as NPDK catalyzes phosphoryl transfer using ATP as the phosphoryl donor and GDP as the acceptor, thereby forming GTP and ADP, respectively. Pyruvate kinase then catalyzes the reaction between the ADP that is formed and the added PEP to form pyruvate and to regenerate ATP. Finally, lactate dehydrogenase catalyzes the reduction of pyruvate as it is formed, and oxidizes NADH to NAD+ in the process. As with the other methods, monitoring the decrease of NADH absorbance or fluorescence with time (i.e., the consumption of NADH) can be utilized to determine the activity of the target protein in real time.

Other methods for screening for modulators of target proteins that directly or indirectly produce GDP from GTP do not utilize enzymatic assays but instead measure the presence of detectable product that is formed by reaction of inorganic phosphate or GDP with a reagent. Such screening methods also initially involve contacting a target protein and a candidate agent under conditions in which, in the absence of the candidate agent, the target protein can produce GDP or inorganic phosphate. The GDP or inorganic phosphate that is formed is then reacted with a reagent that reacts either with GDP or inorganic phosphate to form a detectable product. Detection of the detectable product is thus a measure of the GDP or inorganic phosphate present in the sample, and thus indirectly a measure of the activity of the target protein in converting GTP to GDP and inorganic phosphate.

In many methods of this general type, the reagent that is reacted with GDP or the inorganic phosphate contains a detectable label such as one of types listed above. In other methods, however, the reagent does not include a detectable label but instead the reaction of the reagent with GDP or inorganic phosphate is sufficient in itself to result in the formation of a detectable signal.

Certain methods of this general type utilize reactions in which the inorganic phosphate produced by the target protein is detected using one of a number of different phosphate assays (see below).

C. Non-NADH Coupled Enzyme Assays to Detect GDP Production

Some assays of this type generally involve coupling the conversion of GDP to GTP to the formation of a detectable compound (e.g., a fluorescent compound) that is other than NADH or NAD+. In some assays, for instance, the conversion of GDP to GTP involves the concomitant conversion of a phosphorylated compound to a dephosphorylated compound. The formation of the dephosphorylated compound in turn is coupled to the formation of the detectable compound.

An example of this type of assay generally involves combining a target protein and an enzyme that can utilize the GDP produced directly or indirectly by the target protein. Utilization of GDP by the enzyme is coupled to the conversion of a phosphorylated substrate to a dephosphorylated substrate by the enzyme, thereby resulting in the regeneration of GTP. The oxidation of the dephosphorylated substrate is then coupled to the reduction of an oxidized substrate to form a reduced substrate. Finally, the reduced substrate is oxidized in another enzymatic reaction, with the concomitant reduction of a dye molecule (e.g., fluorophore) to form the detectable compound.

Some assays that fall into this general class are based upon the surprising finding that pyruvate kinase can also be utilized to catalyze the reaction between PEP and GDP to form pyruvate and GTP, respectively, if higher levels of pyruvate kinase are utilized as compared to those utilized when ADP is the substrate. As noted above, the ability to utilize pyruvate kinase to convert GDP to GTP is surprising because of the significantly lower affinity of pyruvate kinase for GDP as compared to ADP. It was thus not expected that a pyruvate kinase reaction with GDP could be utilized to accurately detect the production of GDP, particularly in a kinetic assay format. The pyruvate kinase concentration in assays of this type tends to be about 5-10 times higher than those utilized in ADP assays. Typical pyruvate concentrations in the GDP assays thus are generally about 15-30 U/ml.

In some methods, the GDP produced by the target enzyme is converted back to GTP in a phosphoryl transfer reaction in which pyruvate is also formed (e.g., in a pyruvate kinase reaction). The oxidation of the pyruvate is in turn coupled to the formation of the detectable product. In certain assays of this type, the utilization of GDP produced by the target protein is coupled to the formation of a detectable compound that has a high extinction coefficient (e.g., at least 30,000 $M^{-1}$ $cm^{-1}$, 40,000 $M^{-1}$ $cm^{-1}$, 50,000 $M^{-1}cm^{-1}$, or 60,000 $M^{-1}$ $cm^{-1}$, or any range therebetween).

Figure 4:
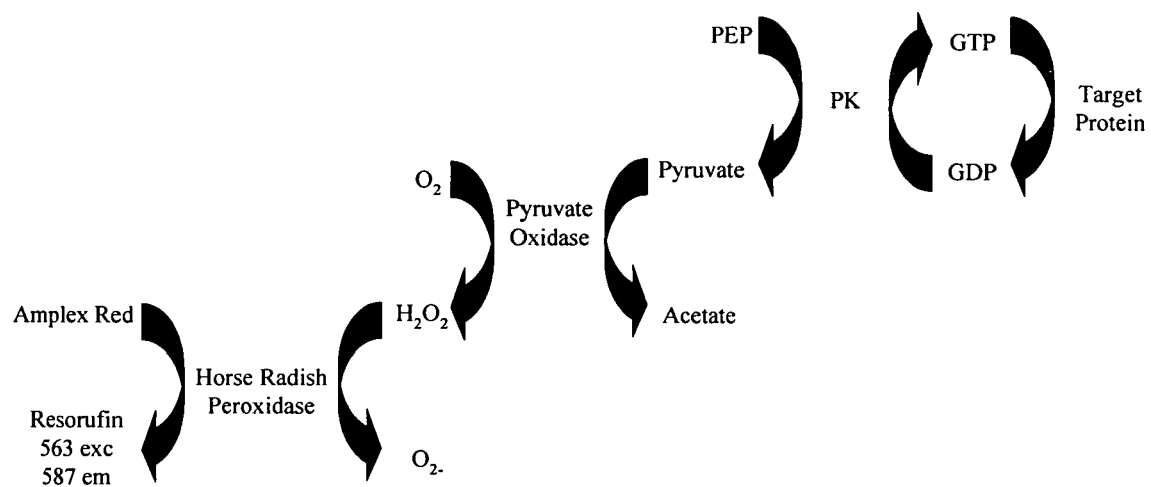
FIG. 4 illustrates another exemplary enzyme coupled assay system that can be utilized to assay for the production of GDP by a target protein that directly or indirectly produces GDP. The assay can be utilized in screening methods to identify modulators of the target protein by conducting the assay, for example, in the presence and absence of a candidate agent. This particular system utilizes pyruvate kinase to regenerate GTP and couples the oxidation of pyruvate to the conversion of AMPLEX RED (Molecular Probes, Inc., Eugene, Oreg.) to Resorufin.

FIG. 4 depicts a specific example of an approach in which pyruvate kinase is utilized to regenerate GTP, with this reaction being coupled to the formation of a fluorescent molecule with a high extinction coefficient. This assay is similar to that depicted in FIG. 3, but takes advantage of the surprising finding that pyruvate kinase at sufficiently high concentrations can be used to catalyze the conversion of GDP to GTP. As indicated in FIG. 4, GTP, pyruvate kinase, PEP, pyruvate oxidase, a peroxidase (e.g., horse radish peroxidase) and 10-acetyl-3,7-dihydroxyphenoxazine (AMPLEX RED, Molecular Probes, Inc., Eugene, Oreg.) are combined to form an assay mixture. The pyruvate kinase in the assay solution catalyzes phosphoryl transfer from PEP to GDP to produce pyruvate and to regenerate GTP. The oxidation of the pyruvate that is formed is in turn coupled to the reduction of oxygen to hydrogen peroxide via the enzymatic activity of pyruvate oxidase. The oxidation of the resulting hydrogen peroxide to superoxide is coupled to the reduction of 10-acetyl-3,7-dihydroxyphenoxazine to form highly fluorescent 3H-phenoxazin-3-one, 7-hydroxy (RESORUFLN, Molecular Probes, Inc., Eugene, Oreg.), which can be detected at a wavelength of 587 nm.

As noted above, although the assays of this type can be conducted with pyruvate oxidases from various sources, pyruvate oxidase from *Lactobacillus plantarum* (Sigma) in combination with phosphate ion cofactor has unexpectedly been found to give improved sensitivity relative to other pyruvate oxidases. As indicated, pyruvate oxidases that utilize phosphate as a cofactor convert pyruvate to acetyl phosphate rather than acetate as shown in FIG. 4.

The assays can be conducted using two mixes such as described above with respect to the ADP assays, with the primary exception being that GTP is substituted for ATP and that the pyruvate kinase concentration is typically increased to about 10 U/mL. Further details regarding such assays are provided in Example 5. Using dyes such as 10-acetyl-3,7-dihydroxyphenoxazine and pyruvate oxidase from *Lactobacillus plantarum* sensitivities can in some instances be improved by about 50, 100 or 200-fold relative to certain assays that monitor NADH consumption.

VII. Exemplary Phosphate Assays

Instead of detecting the formation of ADP or GDP produced by the target protein, the production of phosphate ion can instead be detected. There are also a number of reactions which utilize phosphate. Examples of such reactions include a purine nucleoside phosphorylase reaction. This reaction can be measured directly or indirectly. The reaction can be measured directly by conventional methods known in the art.

In some embodiments, the level of activity of the enzymatic reaction which uses phosphate as a substrate is measured indirectly by being coupled to another reaction. For example, in one embodiment, the method further comprises a purine analog cleavage reaction under conditions which normally allow the cleavage of the purine analog. Webb et al., PNAS 89:4884-4887 (1992); Rieger et al., Anal. Biochem. 246:86-95 (1997); Banik et al., Biochem. J. 266:611-614 (1990). Alternatively, xanthine oxidase can be used in conjunction with purine nucleoside phosphorylase to couple phosphate production to a change in the absorbance of a substrate for xanthine oxidase. Ungerer et al., Clin. Chim. Acta. 223:149-157 (1993).

Instead of using enzymatic assays in which ADP or GDP, for example, is coupled to the production of a detectable product, other non-enzymatic approaches can be utilized. In some embodiments, for instance, the detection of ADP, GDP or phosphate proceeds non-enzymatically, for example by binding or reacting the ADP, GDP or phosphate that is formed by the target protein with a detectable compound. For example, phosphomolybdate based assays can be used which involve conversion of free phosphate to a phosphomolybdate complex. Fiske et al., J. Biol. Chem. 66:375-400 (1925). One method of quantifying the phosphomolybdate is with malachite green. Itaya and Ui, Clin. Chim. Acta 14:361-366 (1966). Alternatively, a fluorescently labeled form of a phosphate binding protein, such as the *E. coli* phosphate binding protein, can be used to measure phosphate by a shift in its fluorescence.

VIII. Exemplary Screens to Identify Modulators of the Polymerization State of Filament Proteins Another exemplary set of screening methods that are provided herein are designed to identify candidate agents that affect the polymerized state of cytoskeletal filament proteins (e.g., actin or tubulin), instead of identifying agents that modulate the activity of a target protein. These assays thus can be utilized, for example, to screen for candidate agents that modulate the polymerization or depolymerization state of filament proteins such as actin or tubulin. In this example, the candidate agent or mixture comprising at least one candidate agent is incubated with the filament protein under conditions that would normally promote either polymerization or depolymerization. A molecular motor that is activated by the filament is then added to the assay mixture and its activity is monitored by ADP or phosphate release as discussed above. Candidate agents which increase the fraction of the filament protein in a polymerized state will be identified by an increase in the motor ATPase and those which increase the fraction of the filament protein in a depolymerized state will be identified by a decrease in the motor ATPase.

IX. Exemplary Protein/Protein Interaction Assays

The invention further provides methods for identifying whether any two test proteins interact. Briefly, the assay is functionally similar to a yeast two-hybrid system, but relies on an increase in ATPase or GTPase activity as a result of bringing two components together as a result of a protein-protein interaction. As an example of the general approach, a system is described that uses a biological polymer binding site and a polymer stimulated ATPase. It will be appreciated by those skilled in the art, however, that any two components that result in an increase in ATPase or GTPase activity as a result of association can be used.

In this particular example, a first test protein (a "bait" protein), for which an interaction is sought, is joined, usually covalently, to a biological polymer binding protein, for example a cytoskeletal binding protein (such as a microtubule binding protein) to form a first target chimera. The term "chimera" or "fusion protein" as used herein refers to a protein (polypeptide) composed of two polypeptides that, while typically unjoined in their native state, typically are joined by their respective amino and carboxyl termini through a peptide linkage to form a single continuous polypeptide. It will be appreciated that the two polypeptide components can be directly joined or joined through a peptide linker/spacer.

A second test protein (a "prey" protein) is joined, again usually covalently, to an ATPase domain that is stimulated by the cytoskeletal component to form a second target chimera. Upon combination with the cytoskeletal component, the first target chimera binds to the cytoskeletal component, and if the first and second target proteins interact, the second target chimera is brought into proximity with the cytoskeletal component, and thus the ATPase activity is stimulated and can be detected. If there is no interaction, no increase in ATP production is observed.

In certain embodiments, the biological polymer binding protein comprises just a domain of a larger protein that comprises an ATPase domain; that is, the ATPase domain has been removed. Alternatively, the biological polymer binding protein may include the larger protein but have the ATPase domain inactivated, for example by mutation. Similarly, the ATPase domain may be either just the ATPase functional domain of a protein, or it may include a larger protein that has the binding domain inactivated.

As discussed above, the chimera proteins are generally joined covalently, for example by making fusion proteins, although covalent cross-linking can be used, or high affinity non-covalent associations can also be done, for example using binding partners such as biotin/avidin, etc. In some embodiments, the fusion proteins are made using fusion genes, as is generally known in the art.

In an embodiment, the target proteins should not have ATPase activity themselves, although it is possible to detect increases in activity.

Suitable biological polymers include, but are not limited to, nucleic acids including DNA and RNA, and cytoskeletal components including, but not limited to, microtubules and microfilaments (actin filaments).

Suitable biological binding sites include, but are not limited to, nucleic acid binding domains (when nucleic acids are the biological polymer), and molecular motor binding domains (in the case of cytoskeletal components).

Suitable ATPases include, but are not limited to, those that exhibit an increase (stimulation) in the presence of the biopolymer, such as DNA and RNA polymerases in the case of nucleic acids, microtubule stimulated ATPases in the case of microtubules including kinesins and dyneins, and actin stimulated ATPases such as myosins.

In some embodiments, the first test protein is attached to a functional molecular motor binding domain to provide a first target chimera. The second test protein is attached to a functional microtubule-stimulated ATPase domain to form a second target chimera. The first and second target chimeras are combined under conditions which normally allow activity of a motor protein which comprises a molecular motor binding domain and a microtubule stimulated ATPase domain. An increase in motor protein activity indicates interaction between the two test proteins.

Customarily one bait protein is used to test a library of test sequences as is described below; however, as will be appreciated by those in the art, the bait protein may be one of a library as well, thus forming an experimental matrix wherein two libraries (although the coding regions of the libraries could be identical) are evaluated for protein-protein interactions. In some embodiments, self-activating bait proteins are filtered out from the bait protein library.

In another embodiment, a method for identifying whether a candidate agent is a modulator of at least one of a first and second test protein is provided. In this case, a candidate agent is combined with the first and second chimeras as described above. A change in molecular motor activity in the presence and absence of the candidate agent indicates that the candidate agent is a modulator of at least one of the two candidate agents.

Thus, the chimeras of the present invention can be formed using recombinant techniques known in the art. The chimera can be formed at the protein level wherein two polypeptides are joined, or at the molecular level wherein a nucleic acid is formed which encodes the appropriate functional motor component and the appropriate test protein.

In some embodiments, the nucleic acids encoding a chimera are used to express the respective recombinant chimera. A variety of expression vectors, including viral and non-viral expression vectors, can be made which are useful for recombinant protein expression in a variety of systems, including, but not limited to, yeast, bacteria, archaebacteria, fungi, insect cells and animal cells, including mammalian cells.

The expressed chimera may also include further fusion domains including tag polypeptides. Recombinant protein is produced by culturing a host cell transformed with a nucleic acid encoding the chimera (generally as an expression vector), under the appropriate conditions that induce or cause expression of the chimera.

In an embodiment, the recombinant chimera is purified following expression, as outlined above.

For using the chimeras in the assays described herein, if the two test proteins bind to one another, a complex with both chimeras comprising a functional molecular motor is formed. Thus, the binding interaction between the two test proteins can be identified by functional motor activity under conditions which would normally allow motor activity if both a functional microtubule stimulated ATPase and binding domain were present.

In the case of identifying a modulator in an assay utilizing the chimeras of the present invention, the modulator can be an activator of the motor activity. Thus, in the absence of the candidate agent, there may be no motor activity; however, in the presence of the candidate agent, motor activity occurs. Conversely, there may be significant motor activity, indicating that the two test binding proteins interact, but this may decrease in the presence of a candidate agent. In either case, the candidate agent is identified as a modulator of at least one the two test proteins.

In some embodiments, motor activity is identified by ATP hydrolysis as described above. However, it is understood that motor activity can be identified by a number of assays. Such assays include microtubule gliding, depolymerization/polymerization and any motor activity which requires both binding and ATPase activity. Therefore, in the case that the molecular motor used has another specific activity, such as involvement in mitosis or axonal transport, specific assays for those activities can be utilized.

Generally motility assays involve immobilizing one component of the system (e.g., the kinesin motor or the microtubule) and then detecting movement, or change thereof, of the other component. Thus, for example, in an embodiment, the microtubule will be immobilized (e.g., attached to a solid substrate) and the movement of the kinesin motor molecule(s) will be visually detected. Typically the molecule that is to be detected is labeled (e.g., with a fluorescent label) to facilitate detection.

Methods of performing motility assays are well known to those of skill in the art (see, e.g., Hall et al., 1996, Biophys. J. 71: 3467-3476; Turner et al., 1996, Anal. Biochem. 242 (1): 20-5; Gittes et al., 1996, Biophys. J. 70(1): 418-29; Shirakawa et al., 1995, J. Exp. Biol. 198: 1809-15; Winkelmann et al., 1995, Biophys. J. 68: 2444-53; Winkelmann et al., 1995, Biophys. J. 68: 72S, and the like).

In addition to the assays described above for identifying ATPase activity, conventional methods can be used. For example, Pi release from kinesin can be quantified. In one embodiment, the ATPase activity assay utilizes 0.3 M PCA (perchloric acid) and malachite green reagent (8.27 mM sodium molybdate II, 0.33 mM malachite green oxalate, and 0.8 mM Triton X-100). To perform the assay, 10 μl of reaction is quenched in 90 μL of cold 0.3 M PCA. Phosphate standards are used so data can be converted to mM inorganic phosphate released. When all reactions and standards have been quenched in PCA, 100 μL of malachite green reagent is added to the relevant wells in e.g., a microtiter plate. The mixture is developed for 10-15 minutes and the plate is read at an absorbance of 650 nm. If phosphate standards are used, absorbance readings can be converted to mM Pi and plotted over time.

Additionally, in the case of methods provided herein utilizing the chimeras in accordance with the present invention, the remaining ATP can be measured using the luciferin-luciferase system. Balharry and Nicholas, Anal. Biochem. 40:1-17 (1971).

The assays are preferably performed in a high throughput system as described herein utilizing multiwell plates and fluorescence or absorbance readouts.

X. Kits

Kits for conducting the assays or screening methods that are disclosed herein are also provided. The kits in general include the assay components necessary to detect the formation or use of ADP, GDP and/or inorganic phosphate. The components making up the kits are typically included in individual containers or combined in a container so long as they are non-reactive with one another.

Some kits for assaying for ADP or GDP, for instance, include one, some or typically all of the following: pyruvate kinase, PEP, LDH and NADH. These kits can also include solutions containing metal ion cofactors (e.g., magnesium chloride and/or manganese chloride). Such kits can be used, for example, to conduct the assays shown in FIG. 1.

Other kits that are useful for assaying for the GDP include one, some or typically all of the following: NPDK, PK, PEP, LDH, and NADH. These kits also can include solutions of the necessary metal ions. Kits of this type can be used, for instance, in performing assays of the type shown in FIG. 2.

Still other kits are include one, some or all of the following components: ATP or GTP, PK, a pyruvate oxidase (e.g., from *Lactobacillus plantarum*), and a peroxidase enzyme (e.g., horse radish peroxidase). If pyruvate oxidase is included in the kit, the kit can also include a phosphate salt (e.g., sodium or potassium phosphate, either mono or dibasic) as a cofactor. A dye such as 10-acetyl-3,7-dihydroxyphenoxazine or other dye with a high extinction coefficient can also be included in some kits. These kits can be used to conduct assays of the type shown in FIG. 3 or 4.

The kits can also include one or more of the following: instructions, an antifoaming agent, a buffering agent, a surfactant, and a multiwell assay plate.

The following examples are provided to illustrate certain aspects of the methods described herein in greater detail. The examples thus should not be construed to limit the claimed invention.

EXAMPLE 1

A High Throughput Assay for Modulators of the Molecular Motor Kinesin

This assay is based on detection of ADP production from kinesin's microtubule stimulated ATPase. ADP production is monitored by a coupled enzyme system consisting of pyruvate kinase and lactate dehydrogenase. Under the assay conditions described below, pyruvate kinase catalyzes the conversion of ADP and phosphoenolpyruvate to pyruvate and ATP. Lactate dehydrogenase then catalyzes the oxidation-reduction reaction of pyruvate and NADH to lactate and NAD+. Thus, for each molecule of ADP produced, one molecule of NADH is consumed. The amount of NADH in the assay solution is monitored by measuring light absorbance at a wavelength of 340 nm.

A. Assay Components

A kinesin heavy chain construct consisting of the N-terminal 420 amino acids is used in the assay. The final 25 µl assay solution consists of the following: 5 µg/ml kinesin, 30 µg/ml microtubules, 5 µM Taxol, 0.8 mM NADH, 1.5 mM phosphoenolpyruvate, 3.5 U/ml pyruvate kinase, 5 U/ml lactate dehydrogenase, 25 mM Pipes/KOH pH 6.8, 2 mM $MgCl_2$, 1 mM EGTA, 1 mM DTT, 0.1 mg/ml BSA, 0.001% antifoam 289 (Sigma), and 1 mM ATP.

B. Compound Plates

Potential chemical modulators of kinesin are dissolved in DMSO at a concentration of approximately 1 mg/ml, and 0.5 µl of each chemical solution is dispensed into a single well of a clear 384 well plate (Clinipate, Labsystems). On each plate, there are at least 16 wells into which pure DMSO (without a candidate compound) is dispensed. These wells serve as negative controls for comparison to the potential chemical modulators on that plate. The compound plates are made in advance and stored at 4° C., and each plate is labeled with a bar code which is used to identify the compounds on a given plate.

C. Instrumentation

The robotic system that runs the assay consists of a plate storage and retrieval device (Plate Stak, CCS Packard), a 96 channel automated pipetting device (Multimek, Beckman), a robotic arm (Twister, Zymark), and a plate reader for absorbance (Ultramark, BioRad). The system is controlled by a custom-built software application.

D. Assay Performance

A stack of compound plates is placed in the plate storage devices and plates are transferred one at a time to the automated pipetting device by the plate carrier of the Plate Stak. Each of the 384 wells are then filled with 20 µl of a solution consisting of all of the assay components described above except for ATP. The plate is then agitated at high frequency by rapidly moving the plate carrier between two positions that are separated by a few millimeters. The plate is then returned to the pipetting position. While the shaking of the plate occurs, the pipet tips are washed with a solution of 0.001% antifoam in deionized water. To start the assay, 5 µl of a second solution containing ATP is then added to each well. The solution is then mixed by a second cycle of high frequency agitation. The plate is then transferred to the plate reader by the robotic arm. In the plate reader, 10 absorbance measurements at 340 nm are taken at 12 second intervals to produce a 2 minute kinetic read for each well. While one plate is being read, the next plate is transferred to the pipetting device and prepared up to but not including the addition of the second solution. When the plate read is complete, the robotic arm transfers the plate to a waste chute and simultaneously the second solution is pipetted into the next plate so that it can be transferred to the reader to complete the cycle. The entire assay is run at room temperature (about 20° C.).

E. Data Analysis

Following data acquisition, the maximum rate of the absorbance change is calculated for each well and normalized to the average of the control wells (without compound) which were present on the same plate. The normalized rates are then entered into an Oracle database, and this allows them to be correlated with the potential chemical modulators. On each plate, the coefficient of variation of the slopes for the control wells ranges from 4-8%. Quality control is assured by monitoring for a minimal initial absorbance and a linear absorbance change.

F. Features

The kinetic design which consists of multiple absorbance measurements improves the specificity of the assay over a single endpoint measurement. First, the rate of the reaction is to a first approximation independent of small differences between wells in the time from the start of the reaction to the first reading, and as a result, the overall variation in the data is reduced. Second, the rate of the absorbance change is not affected by having a chemical compound which absorbs light of the same wavelength.

The presence of control wells in each plate and the subsequent normalization of the data to those wells allows data to be taken for several hours despite some degradation of the enzyme activities which results from the aging of the solutions. This also improves the reproducibility of the data.

The presence of antifoam in the solution and the tip washing solution improves overall liquid handling by reducing the number of trapped bubbles in the small wells and helps flatten the fluid meniscus in each well for more reliable absorbance measurements. Additional features which improve liquid handling are the vigorous shaking of the plate described above, and the round shape of the wells in the microplates used.

The assay components and the performance of the assay are optimized together to match the overall read time with the rate of kinesin's ADP production. In this example, the rate of absorbance change is approximately 150-250 mOD/min. This corresponds to the production of approximately 2 µM ADP/sec. In addition to optimizing the rate of ADP production, the read time must be long enough for the rate of NADH consumption to reach steady state beyond an initial lag time of several seconds. In some cases, the order of addition of the reagents can have a significant affect on the rate of ADP production. In the above example, the optimal rate is achieved by premixing all reagents except for the compound of interest and ATP.

EXAMPLE 2

A High Throughput Assay for Modulators of Bacterial Cytoskeletal Protein FtsZ

This assay is based on detection of GDP production from FtsZ as it polymerizes. GDP production is monitored by a coupled enzyme system consisting of pyruvate kinase and lactate dehydrogenase. Under the assay conditions described below, pyruvate kinase catalyzes the conversion of GDP and phosphoenol pyruvate to pyruvate and GTP. Lactate dehydrogenase then catalyzes the oxidation-reduction reaction of pyruvate and NADH to lactate and NAD+. Thus, for each molecule of GDP produced, one molecule of NADH is consumed. The amount of NADH in the assay solution is monitored by measuring light absorbance at a wavelength of 340 nm.

A. Assay Components

An *E. coli* FtsZ construct consisting of the N-terminal 383 amino acids is used in the assay. The final 25 µl assay solution consists of the following: 100 µg/ml FtsZ, 30 µg/ml microtubules, 0.8 mM NADH, 1.5 mM phosphoenol pyruvate, 17.5 U/ml pyruvate kinase, 5 U/ml lactate dehydrogenase, 25 mM Pipes/KOH pH 6.8, 2 mM $MgCl_2$, 1 mM EGTA, 1 mM DTT, 0.1 mg/ml BSA, 0.001% antifoam 289 (Sigma), and 1 mM GTP.

B. Compound Plates

Potential chemical modulators of FtsZ are dissolved in DMSO at a concentration of approximately 1 mg/ml, and 0.5 µl of each chemical solution is dispensed into a single well of a clear 384 well plate (Clinipate, Labsystems). On each plate, there are at least 16 wells into which pure DMSO (without a candidate compound) is dispensed. These wells serve as negative controls for comparison to the potential chemical modulators on that plate. The compound plates are made in advance and stored at 4° C., and each plate is labeled with a bar code which is used to identify the compounds on a given plate.

C. Instrumentation

The robotic system that runs the assay consists of a plate storage and retrieval device (Plate Stak, CCS Packard), a 96 channel automated pipetting device (Multimek, Beckman), a robotic arm (Twister, Zymark), and a plate reader for absorbance (Ultramark, BioRad). The system is controlled by a custom-built software application.

D. Assay Performance

A stack of compound plates is placed in the plate storage devices and plates are transferred one at a time to the automated pipetting device by the plate carrier of the Plate Stak. Each of the 384 wells are then filled with 12.5 µl of a solution consisting of all of the assay components described above except for ATP. The plate is then agitated at high frequency by rapidly moving the plate carrier between two positions that are separated by a few millimeters. The plate is then returned to the pipetting position. While the shaking of the plate occurs, the pipet tips are washed with a solution of 0.001% antifoam in deionized water. To start the assay, 12.5 µl of a second solution containing GTP is then added to each well. The solution is then mixed by a second cycle of high frequency agitation. The plate is then transferred to the plate reader by the robotic arm. In the plate reader, 18 absorbance measurements at 340 nm are taken at 48 second intervals to produce a kinetic read for each well. While one plate is being read, the next plate is transferred to the pipetting device and prepared up to but not including the addition of the second solution. When the plate read is complete, the robotic arm transfers the plate to a waste chute and simultaneously the second solution is pipetted into the next plate so that it can be transferred to the reader to complete the cycle. The entire assay is run at room temperature about 20° C.

E. Data Analysis

Following data acquisition, the maximum rate of the absorbance change is calculated for each well and normalized to the average of the control wells (without compound) which were present on the same plate. The normalized rates are then entered into an Oracle database, and this allows them to be correlated with the potential chemical modulators. On each plate, the coefficient of variation of the slopes for the control wells ranges from 4-8%. Quality control is assured by monitoring for a minimal initial absorbance and a linear absorbance change.

F. Features

The kinetic design which consists of multiple absorbance measurements improves the specificity of the assay over a single endpoint measurement. First, the rate of the reaction is to a first approximation independent of small differences between wells in the time from the start of the reaction to the first reading, and as a result, the overall variation in the data is reduced. Second, the rate of the absorbance change is not affected by having a chemical compound which absorbs light of the same wavelength.

The presence of control wells in each plate and the subsequent normalization of the data to those wells allows data to be taken for several hours despite some degradation of the enzyme activities which results from the aging of the solutions. This also improves the reproducibility of the data.

The presence of antifoam in the solution and the tip washing solution improves overall liquid handling by reducing the number of trapped bubbles in the small wells and helps flatten the fluid meniscus in each well for more reliable absorbance measurements. Additional features which improve liquid handling are the vigorous shaking of the plate described above, and the round shape of the wells in the microplates used.

The assay components and the performance of the assay are optimized together to match the overall read time with the rate of kinesin's ADP production. In this example, the rate of absorbance change is approximately 15-25 mOD/min. This corresponds to the production of approximately 200 nM GDP/sec. In addition to optimizing the rate of GDP production, the read time must be long enough for the rate of NADH consumption to reach steady state beyond an initial lag time of several seconds. In some cases, the order of addition of the reagents can have a significant affect on the rate of ADP production. In the above example, the optimal rate is achieved by premixing all reagents except for the compound of interest and GTP.

EXAMPLE 3

A High Throughput Assay for Modulators of the Motor Protein KSP

This assay was based on the detection of ADP production from the microtubule stimulated ATPase activity of the motor protein KSP. ADP production was monitored by a coupled enzyme system that included pyruvate kinase, pyruvate oxidase and horse radish peroxidase. Under the assay conditions described in this section, pyruvate kinase catalyzes the reaction between ADP and PEP to form ATP and pyruvate, respectively. Pyruvate oxidase then catalyzes an oxidation/reduction reaction between pyruvate and oxygen to form acetate and hydrogen peroxide. The horse radish peroxidase subsequently catalyzes the oxidation/reduction reaction between hydrogen peroxide and the dye AMPLEX RED (10-acetyl-3, 7-dihydroxyphenoxazine) from Molecular Probes to form the highly fluorescent molecule 3H-phenoxazin-3-one, 7-hydroxy (RESORUFIN, Molecular Probes, Eugene, Oreg.), which can be detected at 587 nm.

A. Assay Components

A KSP ATPase (motor domain of human Ksp—residues M1 to L360) produced at Cytokinetics was used in the assay. The final 25 µl of assay solution contains the following: 0.4 µg/ml KSP, 100 µg/ml microtubules assembled from porcine brain tubulin prepared at Cytokinetics, 6.8 µg/ml pyruvate kinase (Sigma), 4 U/ml pyruvate oxidase (Sigma), 0.5 U/ml horse radish peroxidase (Sigma), 0.25 mM ATP, 0.1 mM PEP, 0.05 mM AMPLEX RED, 5 µM paclitaxel, 50 ppm antifoam 298 (Sigma) and 0.1 mg/ml BSA in 25 mM Pipes buffer, pH 6.8, 2 mM $MgCl_2$.

The assays solutions were prepared as indicated in the following Table 1:

|  | Stock | In Assay |
|---|---|---|
| Common Members |  |  |
| Paclitaxel | 10 mM | 5 µM |
| Antifoam | 10% | 50 ppm |
| BSA | 20 mg/mL | 0.1 mg/mL |
| Pipes | 50 mM | 25 mM |
| $MgCl_2$ | 1000 mM | 2 mM |
| Potassium Phosphate | 200 mM | 2 mM |
| Solution 1 |  |  |
| ATP | 100 mM | 0.25 mM |
| PEP | 50 mM | 0.1 mM |
| Amplex Red | 10 mM | 0.05 mM |
| KSP | 3.6 mg/ml | 0.4 µg/mL |
| Solution 2 |  |  |
| Pyruvate Kinase (PK) | 3.4 mg/ml | 6.8 µg/ml |
| Microtubules |  | 100.00 µg/mL |
| Puruvate Oxidase | 100.00 | 4.00 U/mL |
| Horse Radish Peroxidase | 1000.00 | 0.50 U/mL |

B. Compound Plates/Instrumentation

Potential chemical modulators of KSP were dissolved in DMSO at a concentration of approximately 1 mg/ml, and 0.5 µl of each solution dispensed into a single well of a clear 384 well plate (Clinipate, Labsystems). On each plate, there are at least 16 wells into which pure DMSO (without a candidate compound) is dispensed. These wells serve as negative controls for comparison to the potential chemical modulators on that plate. The compound plates are made in advance and stored at 4° C., and each plate is labeled with a bar code which is used to identify the compounds on a given plate.

The same type of instrumentation as described in Example 1 was utilized in performing this investigation.

C. Assay Performance

A stack of compound plates is placed in the plate storage devices and plates are transferred one at a time to the automated pipetting device by the plate carrier of the Plate Stak. Each of the 384 wells is then filled with 12.5 µl of solution 2 listed in Table 1 (supra). The pipet tips are washed with a solution of 0.001% antifoam in deionized water. To start the assay, 12.5 µl of solution 1 is then added to each well. The solution is then mixed by pipetting the solution up and down 10 times. The plate is then transferred to the plate reader by the robotic arm. In the plate reader, the plate is exposed to 563 nm light to excite AMPLEX RED and 10 fluorescence measurements at 587 nm are taken at 50 second intervals to produce a 8 minute kinetic read for each well. While one plate is being read, the next plate is transferred to the pipetting device and prepared up to but not including the addition of the second solution. When the plate read is complete, the robotic arm transfers the plate to a waste chute and simultaneously the second solution is pipetted into the next plate so that it can be transferred to the reader to complete the cycle. The entire assay is run at room temperature about 20° C.

D. Data Analysis

Following data acquisition, the maximum rate of the fluorescence change is calculated for each well and normalized to the average of the control wells (without compound) which were present on the same plate. The normalized rates are then entered into an Oracle database, and this allows them to be correlated with the potential chemical modulators. On each plate, the coefficient of variation of the slopes for the control wells ranges from 4-8%. Quality control is assured by monitoring for a minimal initial absorbance and a linear absorbance change.

E. Features

The kinetic design, use of control wells and antifoam agents provides the benefits described in Example 1. The improved sensitivity possible using dyes such as AMPLEX RED means that very low ATPase activity can be measured using assays such as described in this example and that the amount of reagent consumed in the assays can be reduced by about 100-fold relative to certain NADH-based assays. For instance, ATPase activities as low as about 0.003 $s^{-1}$ can be measured. Furthermore, because the excitation and emission wavelengths are at 560 and 580 nm, respectively, interference from fluorescent compounds that can be problematic in the near UV region is reduced.

The assay components and the performance of the assay are optimized together to match the overall read time with the rate at which ADP is produced by KSP. In this example, the rate of fluorescence intensity change is approximately 25000 RFU/sec. This corresponds to the production of approximately 0.00085 µM ADP/sec. In addition to optimizing the rate of ADP production, the read time should be long enough for the rate of AMPLEX RED consumption to reach steady state beyond an initial lag time of several seconds. In some cases, the order of addition of the reagents can have a significant effect on the rate of ADP production. In this example, the optimal rate is achieved by premixing all reagents except for the compound of interest and ATP.

EXAMPLE 4

A High Throughput Assay for Modulators of Basal ATPase Activity of the Motor Protein KSP This assay was based on the detection of ADP production from the basal ATPase activity of KSP (motor domain of human Ksp—residues M1to L360). ADP production was monitored by a coupled enzyme system that included pyruvate kinase, pyruvate oxidase and horse radish peroxidase. Under the assay conditions described in this section, pyruvate kinase catalyzes the reaction between ADP and PEP to form ATP and pyruvate, respectively. Pyruvate oxidase then catalyzes an oxidation/reduction reaction between pyruvate and oxygen to form acetate and hydrogen peroxide. The horse radish peroxidase subsequently catalyzes the oxidation/reduction reaction between hydrogen peroxide and the dye AMPLEX RED (10-acetyl-3,7-dihydroxyphenoxazine) from Molecular Probes to form the highly fluorescent molecule 3H-phenoxazin-3-one, 7-hydroxy (RESORUFIN, Molecular Probes, Eugene, Oreg.), which can be detected at 587 nm.

A. Assay Components

A KSP ATPase domain produced at Cytokinetics was used in the assay. The final 25 µl of assay solution contains the following: 10 µg/ml KSP, 6.8 µg/ml pyruvate kinase (Sigma), 4 U/ml pyruvate oxidase (Sigma), 0.5 U/ml horse radish peroxidase (Sigma), 0.1 mM ATP, 0.1 mM PEP, 0.05 mM AMPLEX RED, 2 mM Sodium Phosphate, 50 ppm antifoam 298 (Sigma) and 0.1 mg/ml BSA in 25 mM Pipes buffer, pH 6.8, 2 mM $MgCl_2$.

The assays solutions were prepared as indicated in the following Table 2:

|  | Stock | In Assay |
|---|---|---|
| Common Members |  |  |
| Antifoam | 10% | 50 ppm |
| BSA | 20 mg/mL | 0.1 mg/mL |
| Pipes | 50 mM | 25 mM |
| $MgCl_2$ | 1000 mM | 2 mM |
| Sodium Phosphate | 200 mM | 2 mM |
| Solution 1 |  |  |
| ATP | 100 mM | 0.1 mM |
| PEP | 50 mM | 0.1 mM |
| Amplex Red | 10 mM | 0.05 mM |
| Solution 2 |  |  |
| Pyruvate Kinase (PK) | 3.4 mg/ml | 6.8 µg/ml |
| Puruvate Oxidase | 100.00 U/mL | 4.00 U/mL |
| KSP | 3.4 mg/ml | 10 µg/mL |
| Horse Radish Peroxidase | 1000.00 U/mL | 0.50 U/mL |

B. Compound Plates/Instrumentation

Potential chemical modulators of KSP were dissolved in DMSO at a concentration of approximately 1 mg/ml, and 0.5 µl of each solution dispensed into a single well of a clear 384 well plate (Clinipate, Labsystems). On each plate, there are at least 16 wells into which pure DMSO (without a candidate compound) is dispensed. These wells serve as negative controls for comparison to the potential chemical modulators on that plate. The compound plates are made in advance and stored at 4° C., and each plate is labeled with a bar code which is used to identify the compounds on a given plate.

The same type of instrumentation as described in Example 1 was utilized in performing this investigation.

C. Assay Performance

A stack of compound plates is placed in the plate storage devices and plates are transferred one at a time to the automated pipetting device by the plate carrier of the Plate Stak. Each of the 384 wells is then filled with 12.5 µl of solution 2 listed in Table 2. The pipet tips are washed with a solution of 0.001% antifoam in deionized water. To start the assay, 12.5 µl of solution 1 is then added to each well. The solution is then mixed by pipetting the solution up and down 10 times. The plate is then transferred to the plate reader by the robotic arm. In the plate reader, the plate is exposed to 563 nm light to excite AMPLEX RED and 10 fluorescence measurements at 587 nm are taken at 50 second intervals to produce a 8 minute kinetic read for each well. While one plate is being read, the next plate is transferred to the pipetting device and prepared up to but not including the addition of the second solution. When the plate read is complete, the robotic arm transfers the plate to a waste chute and simultaneously the second solution is pipetted into the next plate so that it can be transferred to the reader to complete the cycle. The entire assay is run at room temperature about 20° C.

D. Data Analysis

Following data acquisition, the maximum rate of the fluorescence change is calculated for each well and normalized to the average of the control wells (without compound) which were present on the same plate. The normalized rates are then entered into an Oracle database, and this allows them to be correlated with the potential chemical modulators. On each plate, the coefficient of variation of the slopes for the control wells ranges from 4-8%. Quality control is assured by monitoring for a minimal initial absorbance and a linear absorbance change.

E. Features

The kinetic design, use of control wells and antifoam agents provides the benefits described in Example 1. The improved sensitivity possible using dyes such as AMPLEX RED means that very small ATPase activities can be measured using assays such as described in this example and that the amount of reagent consumed in the assays can be reduced by about 100-fold relative to certain NADH-based assays. For instance, ATPase activities as low as about 0.0004 µM/s can be measured. Furthermore, because the excitation and emission wavelengths are at 560 and 580 nm, respectively, interference from fluorescent compounds that can be problematic in the near UV region is reduced.

The assay components and the performance of the assay are optimized together to match the overall read time with the rate at which ADP is produced by KSP. In this example, the rate of fluorescence intensity change is approximately 9000 RFU/sec. This corresponds to the production of approximately 0.00035 µM ADP/sec. In addition to optimizing the rate of ADP production, the read time should be long enough for the rate of AMPLEX RED consumption to reach steady state beyond an initial lag time of several seconds. In some cases, the order of addition of the reagents can have a significant effect on the rate of ADP production. In this example, the optimal rate is achieved by premixing all reagents except for the compound of interest and ATP.

EXAMPLE 5

A High Throughput Fluorescence Assay for Modulators of FtsZ GTPase Activity

This assay was based on the detection of GDP production from the GTPase activity of the protein FtsZ. GDP production was monitored by a coupled enzyme system that included pyruvate kinase, pyruvate oxidase and horse radish peroxidase. Under the assay conditions described in this section, pyruvate kinase catalyzes the reaction between GDP and PEP to form GTP and pyruvate, respectively. Pyruvate oxidase then catalyzes an oxidation/reduction reaction between pyruvate and oxygen to form acetate and hydrogen peroxide. The horse radish peroxidase subsequently catalyzes the oxidation/reduction reaction between hydrogen peroxide and the dye AMPLEX RED (10-acetyl-3,7-dihydroxyphenoxazine) from Molecular Probes to form the highly fluorescent molecule 3H-phenoxazin-3-one, 7-hydroxy (RESORUFIN, Molecular Probes, Eugene, Oreg.), which can be detected at 587 nm.

A. Assay Components

The protein *E. coli* FtsZ was used in the assay. The final 25 µl of assay solution contains the following: 20 µg/ml FtsZ, pyruvate kinase, 17.5 U/ml pyruvate kinase, 4 U/ml pyruvate oxidase (Sigma), 2 mM sodium phosphate, 0.5 U/ml horse radish peroxidase (Sigma) 0.07 mM GTP, 0.1 mM PEP, 0.05 mM AMPLEX RED, 50 ppm antifoam 298 (Sigma) and 0.1 mg/ml BSA.

B. Compound Plates/Instrumentation

Potential chemical modulators of FtsZ were dissolved in DMSO at a concentration of approximately 1 mg/ml, and 0.5 µl of each solution dispensed into a single well of a clear 384 well plate (Costar, Corning). On each plate, there are at least 16 wells into which pure DMSO (without a candidate compound) is dispensed. These wells serve as negative controls for comparison to the potential chemical modulators on that plate. The compound plates are made in advance and stored at 4° C., and each plate is labeled with a bar code which is used to identify the compounds on a given plate.

The same type of instrumentation as described in Example 1 was utilized in performing this investigation.

C. Assay Performance

A stack of compound plates is placed in the plate storage devices and plates are transferred one at a time to the automated pipetting device by the plate carrier of the Plate Stak. Each of the 384 wells are then filled with 12.5 µl of a solution consisting of all of the assay components described above except for GTP. The plate is then agitated at high frequency by rapidly moving the plate carrier between two positions that are separated by a few millimeters. The plate is then returned to the pipetting position. While the shaking of the plate occurs, the pipet tips are washed with a solution of 0.001% antifoam in deionized water. To start the assay, 12.5 µl of a second solution containing GTP is then added to each well. The solution is then mixed by a second cycle of high frequency agitation. The plate is then transferred to the plate reader by the robotic arm. In the plate reader, the plate is exposed to 480 nm light to excite AMPLEX RED and ten fluorescence measurements at 610 nm are taken at 60 second intervals to produce a 10 minute kinetic read for each well. Note that the off peak excitation and emission is used to maximize the assay window. While one plate is being read, the next plate is transferred to the pipetting device and prepared up to but not including the addition of the second solution. When the plate read is complete, the robotic arm transfers the plate to a waste chute and simultaneously the second solution is pipetted into the next plate so that it can be transferred to the reader to complete the cycle. The entire assay is run at room temperature (about 20° C.).

D. Data Analysis

Following data acquisition, the maximum rate of the fluorescence change is calculated for each well and normalized to the average of the control wells (without compound) which were present on the same plate. The normalized rates are then entered into an Oracle database, and this allows them to be correlated with the potential chemical modulators. On each plate, the coefficient of variation of the slopes for the control wells ranges from 10%. Quality control is assured by monitoring for a minimal initial absorbance and a linear absorbance change.

E. Features

The kinetic design, use of control wells and antifoam agents provides the benefits described in Example 1. The improved sensitivity possible using dyes such as AMPLEX RED as described in Examples 3 and 4 can also be obtained using assays of this type.

The assay components and the performance of the assay are optimized together to match the overall read time with the rate at which GDP is produced by FtsZ. In this example, the rate of fluorescence change is approximately 2000 RFU/min. This corresponds to the production of approximately 0.01 µM GDP/sec. In addition to optimizing the rate of GDP production, the read time should be long enough for the rate of AMPLEX RED consumption to reach steady state beyond an initial lag time of several seconds. In some cases, the order of addition of the reagents can have a significant effect on the rate of GDP production. In this example, the optimal rate is achieved by premixing all reagents except for the compound of interest and GTP.

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entirety for all purposes to the same extent as if each individual publication, patent or patent application were specifically and individually indicated to be so incorporated by reference.

What is claimed is:

1. A method for screening a candidate agent to determine if it is a modulator of the activity of a target protein that can produce adenosine diphosphate (ADP), the method comprising:
   (a) preparing a sample that comprises the target protein, the candidate agent and an enzyme that utilizes ADP under conditions in which, in the absence of the candidate agent, the target protein can produce ADP; and
   (b) determining the activity of the enzyme in the sample to determine the activity of the target protein, wherein the activity of the enzyme is determined by detecting the formation of a detectable compound that is formed in a coupled enzyme system that includes (i) a reaction in which the utilization of ADP by the enzyme results in the formation of pyruvate, (ii) a reaction in which the oxidation of pyruvate results in the formation of hydrogen peroxide, and (iii) a reaction in which the oxidation of hydrogen peroxide results in the conversion of a compound to the detectable compound; and a change in the activity of the enzyme in the presence of the candidate agent relative to the activity of the enzyme in the absence of the candidate agent is an indication that the candidate agent is a modulator of the target protein.

2. The method of claim 1, wherein preparing comprises combining the target protein, the candidate agent and the enzyme with phosphoenolpyruvate (PEP), pyruvate kinase (PK), pyruvate oxidase, phosphate and a peroxidase;

the coupled enzyme system involves (i) pyruvate kinase catalyzing the reaction between PEP and ADP formed by the target protein to form pyruvate and ATP, respectively, (ii) pyruvate oxidase in the presence of phosphate catalyzing the oxidation of pyruvate to acetylphosphate and the concomitant reduction of oxygen to hydrogen peroxide, and (iii) the peroxidase catalyzing the oxidation of hydrogen peroxide to superoxide and the concomitant reaction of the superoxide with the compound to form the detectable compound; and determining is conducted in the form of a kinetic assay in which the activity of the enzyme is determined at multiple time points.

3. The method of claim 2, wherein the pyruvate oxidase is from *Lactobacillus plantrum*.

4. The method of claim 3, wherein the peroxidase is a horse radish peroxidase.

5. The method of claim 2, wherein the detectable compound is a fluorescent compound.

6. The method of claim 5, wherein the fluorescent compound is 3H-phenoxazin-3-one, 7-hydroxy.

7. The method of claim 2, wherein preparing comprises contacting the target protein with a plurality of candidate agents.

8. The method of claim 2, wherein preparing comprises contacting a plurality of target proteins with a plurality of candidate agents.

9. The method of claim 7, wherein preparing comprises preparing a plurality of samples, each sample containing the target protein and one or more of the plurality of candidate agents; and determining comprises determining the activity of the enzyme for each of the plurality of samples.

10. The method of claim 2, wherein the method is repeated with about 10,000 samples per hour.

11. The method of claim 2, wherein the sample further comprises a surfactant or an antifoaming agent.

12. The method of claim 2, wherein preparing is performed with a robotic system.

13. The method of claim 2, wherein the target protein is an ATPase, a kinase, a phosphatase or a phosphorylase.

14. The method of claim 13, wherein the ATPase is a kinesin.

15. The method of claim 14, wherein the kinesin is Kin2, chromokinesin, Kif1A, KSP, CENP-E, MCAK, HSET, RabK6, Kip3D or Kif15.

16. The method of claim 13, wherein the target protein is myosin.

17. The method of claim 13, wherein the target protein is dynein.

18. The method of claim 1, wherein the target protein generates an initial product that regulates the production of ADP by another protein.

19. The method of claim 1, wherein the target protein generates a substrate for an enzyme that in turn produces ADP.

20. The method of claim 1, wherein the target protein is an activator of an ATPase.

21. A method for screening a candidate agent to determine if it is a modulator of the activity of a target protein that can produce adenosine diphosphate (ADP), the method comprising:

(a) preparing a sample that comprises the target protein, the candidate agent, a pyruvate oxidase from *Lactobacillus plantarum*, a phosphate ion cofactor and an enzyme that utilizes ADP, under conditions in which, in the absence of the candidate agent, the target protein can produce ADP; and (b) determining the activity of the enzyme in the sample at multiple time points as part of a kinetic assay to determine the activity of the target protein, wherein the activity of the enzyme is determined by detecting the formation of a detectable compound that is formed in a coupled enzyme system in which (i) the utilization of ADP by the enzyme results in the formation of pyruvate, and (ii) the pyruvate oxidase with the phosphate ion cofactor catalyzes a reaction in which pyruvate is oxidized to acetyl phosphate, which reaction is coupled to the formation of the detectable compound; and a change in the activity of the enzyme in the presence of the candidate agent relative to the activity of the enzyme in the absence of the candidate agent is an indication that the candidate agent is a modulator of the target protein.

* * * * *